United States Patent
Gane et al.

(10) Patent No.: US 10,301,774 B2
(45) Date of Patent: *May 28, 2019

(54) PROCESS FOR THE PRODUCTION OF NANO-FIBRILLAR CELLULOSE SUSPENSIONS

(71) Applicant: FiberLean Technologies Limited, Par Cornwall (GB)

(72) Inventors: Patrick A. C. Gane, Rothrist (CH); Joachim Schoelkopf, Killwangen (CH); Daniel Gantenbein, Elnesvagen (NO); Michel Schenker, Schönenwerd (CH); Michael Pohl, Villach (AT); Beat Kübler, Oberwil (CH)

(73) Assignee: FiberLean Technologies Limited, Par Cornwall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,705

(22) Filed: Sep. 2, 2014

(65) Prior Publication Data
US 2014/0371172 A1 Dec. 18, 2014

Related U.S. Application Data

(63) Continuation of application No. 13/138,647, filed as application No. PCT/EP2010/054231 on Mar. 30, 2010, now Pat. No. 8,871,057.
(Continued)

(30) Foreign Application Priority Data

Mar. 30, 2009 (EP) .................................... 09156683

(51) Int. Cl.
| | | |
|---|---|---|
| *D21B 1/16* | (2006.01) | |
| *D21C 9/00* | (2006.01) | |

(Continued)

(52) U.S. Cl.
CPC ............... *D21C 9/007* (2013.01); *D21B 1/16* (2013.01); *D21D 1/00* (2013.01); *D21H 11/18* (2013.01); *D21H 17/675* (2013.01); *D21H 15/04* (2013.01)

(58) Field of Classification Search
CPC ..... C08K 2003/265; C08K 3/23; C08L 97/02; D21H 11/18
See application file for complete search history.

(56) References Cited

U.S. PATENT DOCUMENTS

| 57,307 A | 8/1866 | Fletcher |
|---|---|---|
| 168,783 A | 10/1875 | Riley |

(Continued)

FOREIGN PATENT DOCUMENTS

| BE | 1006908 A3 | 1/1995 |
|---|---|---|
| CA | 1096676 A | 3/1981 |

(Continued)

OTHER PUBLICATIONS

Turbak, D. F., "Birth of Nanocellulose," online publication from TAPPI, http://www.naylornetwork.com/PPI-OTW/articles/print.asp?aid=150993, undated publication, accessed Nov. 1, 2015.*

(Continued)

*Primary Examiner* — Nicholas E Hill
(74) *Attorney, Agent, or Firm* — Pierce Atwood LLP; Raymond G. Arner

(57) ABSTRACT

The present invention relates to a process for the production of suspensions of nano-fibrillar cellulose by providing cellulose fibers and at least one filler and/or pigment; combining the cellulose fibers and the at least one filler and/or pigment; and fibrillating the cellulose fibers in the presence of at least one filler and/or pigment, as well as the suspensions of nano-fibrillar cellulose obtained by this process and their uses.

39 Claims, 4 Drawing Sheets

Related U.S. Application Data

(60) Provisional application No. 61/212,108, filed on Apr. 6, 2009.

(51) Int. Cl.
*D21D 1/00* (2006.01)
*D21H 11/18* (2006.01)
*D21H 17/67* (2006.01)
*D21H 15/04* (2006.01)

(56) References Cited

U.S. PATENT DOCUMENTS

| | | | |
|---|---|---|---|
| 1,538,257 A | 5/1925 | Obrecht | |
| 2,006,209 A | 5/1933 | Bradner | |
| 2,169,473 A | 2/1935 | Olsen et al. | |
| 2,583,548 A | 1/1952 | Lutton et al. | |
| 3,075,710 A | 1/1963 | Feld et al. | |
| 3,730,830 A | 5/1973 | Driscoll | |
| 3,765,921 A | 10/1973 | Puskar | |
| 3,794,558 A | 2/1974 | Back | |
| 3,820,548 A | 6/1974 | Buchmann et al. | |
| 3,921,581 A | 11/1975 | Brewer | |
| 4,026,762 A | 5/1977 | Bauman | |
| 4,087,317 A | 5/1978 | Roberts | |
| 4,167,548 A | 9/1979 | Arduini et al. | |
| 4,229,250 A | 10/1980 | Lehtinen | |
| 4,275,084 A | 6/1981 | Ohyabu et al. | |
| 4,285,842 A | 8/1981 | Herr | |
| 4,318,959 A | 3/1982 | Evans et al. | |
| 4,341,807 A | 7/1982 | Turbak et al. | |
| 4,356,060 A | 10/1982 | Neckermann et al. | |
| 4,374,702 A | 2/1983 | Turbak et al. | |
| 4,378,381 A | 3/1983 | Turbak et al. | |
| 4,426,258 A | 1/1984 | Browning | |
| 4,452,721 A | 6/1984 | Turbak et al. | |
| 4,452,722 A | 6/1984 | Turbak et al. | |
| 4,460,737 A | 8/1984 | Evans et al. | |
| 4,464,287 A | 8/1984 | Turbak et al. | |
| 4,474,949 A | 10/1984 | Chatterjee et al. | |
| 4,481,076 A | 11/1984 | Herrick | |
| 4,481,077 A | 11/1984 | Herrick | |
| 4,487,634 A | 12/1984 | Turbak et al. | |
| 4,495,245 A | 1/1985 | Zunker | |
| 4,500,546 A | 2/1985 | Turbak et al. | |
| 4,510,020 A | 4/1985 | Green et al. | |
| 4,705,712 A | 11/1987 | Cashaw et al. | |
| 4,744,987 A | 5/1988 | Mehra et al. | |
| 4,761,203 A | 8/1988 | Vinson | |
| 4,820,813 A | 4/1989 | Schulz | |
| 4,889,594 A | 12/1989 | Gavelin | |
| 4,952,278 A | 8/1990 | Gregory et al. | |
| 5,009,886 A | 4/1991 | Ahmad et al. | |
| 5,098,520 A | 3/1992 | Begala | |
| 5,104,411 A | 4/1992 | Makoui et al. | |
| 5,123,962 A | 6/1992 | Komuro et al. | |
| 5,156,719 A | 10/1992 | Passaretti | |
| 5,223,090 A | 6/1993 | Klungness et al. | |
| 5,227,024 A | 6/1993 | Gomez | |
| 5,225,041 A | 7/1993 | Richard et al. | |
| 5,228,900 A | 7/1993 | Stephens et al. | |
| 5,240,561 A | 8/1993 | Kaliski | |
| 5,244,542 A | 9/1993 | Bown et al. | |
| 5,269,470 A | 12/1993 | Ishikawa et al. | |
| 5,274,199 A | 12/1993 | Uryu et al. | |
| 5,279,663 A | 1/1994 | Kaliski | |
| 5,312,484 A | 1/1994 | Kaliski | |
| 5,290,830 A * | 3/1994 | Tung | B60C 1/00 162/13 |
| 5,316,621 A | 5/1994 | Kitao et al. | |
| 5,385,640 A | 1/1995 | Weibel et al. | |
| 5,443,902 A | 1/1995 | Knox et al. | |
| 5,387,319 A | 2/1995 | Mora et al. | |
| 5,487,419 A | 1/1996 | Weibel | |
| 5,531,821 A | 7/1996 | Wu | |
| 5,605,568 A | 2/1997 | Naydowski et al. | |
| 5,670,623 A | 9/1997 | Shoseyov et al. | |
| 5,731,080 A * | 3/1998 | Cousin | D21H 11/18 106/464 |
| 5,840,320 A | 3/1998 | Odom | |
| 5,817,381 A | 11/1998 | Chen et al. | |
| 5,837,376 A | 11/1998 | Knox et al. | |
| 5,964,983 A | 10/1999 | Dinand et al. | |
| 6,037,380 A | 3/2000 | Venables et al. | |
| 6,074,524 A | 3/2000 | Wu et al. | |
| 6,083,317 A * | 7/2000 | Snowden | C09C 1/024 106/464 |
| 6,083,582 A | 7/2000 | Chen et al. | |
| 6,117,305 A | 9/2000 | Bando et al. | |
| 6,117,474 A | 9/2000 | Kameda et al. | |
| 6,117,545 A | 9/2000 | Cavaille et al. | |
| 6,117,804 A | 9/2000 | Cho | |
| 6,132,558 A | 10/2000 | Dyllick-Brenzinger et al. | |
| 6,156,118 A | 12/2000 | Silenius | |
| 6,159,335 A | 12/2000 | Owens et al. | |
| 6,183,596 B1 | 2/2001 | Matsuda et al. | |
| 6,202,946 B1 | 3/2001 | Virtanen | |
| 6,207,436 B1 | 3/2001 | Bjørnvad et al. | |
| 6,214,163 B1 | 4/2001 | Matsuda et al. | |
| 6,235,150 B1 | 5/2001 | Middleton et al. | |
| 6,312,669 B1 | 11/2001 | Cantiani et al. | |
| 6,339,898 B1 | 1/2002 | Toye | |
| 6,379,594 B1 | 4/2002 | Dopfner et al. | |
| 6,436,232 B1 | 8/2002 | Silenius et al. | |
| 6,468,393 B1 | 10/2002 | Small et al. | |
| 6,579,410 B1 | 6/2003 | Bleakley et al. | |
| 6,604,698 B2 | 8/2003 | Verhoff et al. | |
| 6,647,662 B2 | 11/2003 | Toye | |
| 6,669,882 B2 | 12/2003 | Seok | |
| 6,706,876 B2 | 3/2004 | Luo et al. | |
| 6,726,807 B1 | 4/2004 | Mathur | |
| 6,787,497 B2 | 9/2004 | Dellve et al. | |
| 6,861,081 B2 | 3/2005 | Weibel | |
| 7,022,756 B2 | 4/2006 | Singer | |
| 7,048,900 B2 | 5/2006 | Mathur et al. | |
| 7,083,703 B2 | 8/2006 | Aho et al. | |
| 7,169,258 B2 | 1/2007 | Rheims et al. | |
| 7,179,347 B2 | 2/2007 | Rheims et al. | |
| 7,285,182 B2 | 10/2007 | Mason et al. | |
| 7,381,294 B2 | 6/2008 | Suzuki et al. | |
| 7,459,493 B2 | 12/2008 | Singer | |
| 7,462,232 B2 | 12/2008 | Tuason et al. | |
| 7,497,924 B2 | 3/2009 | Nguyen et al. | |
| 7,594,619 B2 | 9/2009 | Ghere, Jr. et al. | |
| 7,726,592 B2 | 6/2010 | Fernandez et al. | |
| 7,790,276 B2 | 9/2010 | Kanakarajan | |
| 7,799,358 B2 | 9/2010 | Weibel | |
| 8,012,312 B2 | 9/2011 | Goto et al. | |
| 8,012,573 B2 | 9/2011 | Kowata et al. | |
| 8,231,764 B2 | 7/2012 | Husband et al. | |
| 8,784,611 B2 * | 7/2014 | Juppo | D21H 21/10 162/157.6 |
| 8,871,056 B2 | 10/2014 | Gane et al. | |
| 8,871,057 B2 | 10/2014 | Gane et al. | |
| 9,157,189 B2 | 10/2015 | Heiskanen et al. | |
| 9,175,442 B2 | 11/2015 | Gane et al. | |
| 9,399,838 B2 | 7/2016 | Laine et al. | |
| 2001/0011516 A1 | 8/2001 | Cantiani et al. | |
| 2001/0045264 A1 | 11/2001 | Rheims et al. | |
| 2002/0031592 A1 | 3/2002 | Weibel | |
| 2002/0059886 A1 | 5/2002 | Merkley et al. | |
| 2002/0198293 A1 | 12/2002 | Craun et al. | |
| 2003/0051841 A1 | 3/2003 | Mathur et al. | |
| 2003/0094252 A1 * | 5/2003 | Sundar | D21H 17/70 162/128 |
| 2003/0114641 A1 | 6/2003 | Kelly et al. | |
| 2004/0108081 A1 | 6/2004 | Hughes | |
| 2004/0131854 A1 | 7/2004 | Aho et al. | |
| 2004/0146605 A1 | 7/2004 | Weibel | |
| 2004/0149403 A1 | 8/2004 | Rheims et al. | |
| 2004/0168782 A1 | 9/2004 | Silenius et al. | |
| 2004/0168783 A1 * | 9/2004 | Munchow | D21H 19/00 162/189 |
| 2004/0173329 A1 | 9/2004 | Silenius et al. | |

(56) References Cited

U.S. PATENT DOCUMENTS

| | | |
|---|---|---|
| 2004/0226671 A1 | 11/2004 | Nguyen et al. |
| 2005/0000665 A1 | 1/2005 | Doelle |
| 2005/0045288 A1 | 3/2005 | Riou |
| 2005/0051054 A1 | 3/2005 | White et al. |
| 2005/0089601 A1 | 4/2005 | Weibel |
| 2005/0103459 A1 | 5/2005 | Mathur |
| 2005/0116010 A1 | 6/2005 | Gronroos et al. |
| 2005/0133643 A1 | 6/2005 | Fernandez et al. |
| 2005/0194477 A1 | 9/2005 | Suzuki |
| 2005/0236121 A1* | 10/2005 | Kondo ................. C08J 3/12 162/100 |
| 2005/0256262 A1 | 11/2005 | Hill et al. |
| 2006/0078647 A1 | 4/2006 | Weibel |
| 2006/0201646 A1 | 9/2006 | Gussinyer Canadell |
| 2006/0266485 A1 | 11/2006 | Knox et al. |
| 2006/0280839 A1 | 12/2006 | Weibel |
| 2006/0289132 A1 | 12/2006 | Heijnesson-Hulten |
| 2007/0062009 A1 | 3/2007 | Ghere, Jr. et al. |
| 2007/0131361 A1 | 6/2007 | Doelle et al. |
| 2007/0148365 A1 | 6/2007 | Knox et al. |
| 2007/0224419 A1 | 9/2007 | Sumnicht et al. |
| 2007/0226919 A1 | 10/2007 | Mheidle |
| 2007/0231568 A1 | 10/2007 | Kanakarajan |
| 2007/0272376 A1 | 11/2007 | Maijala et al. |
| 2008/0023161 A1 | 1/2008 | Gather |
| 2008/0057307 A1 | 3/2008 | Koslow et al. |
| 2008/0060774 A1* | 3/2008 | Zuraw ................. C09D 101/00 162/135 |
| 2008/0146701 A1 | 6/2008 | Sain et al. |
| 2008/0210391 A1 | 9/2008 | Pfalzer et al. |
| 2008/0265222 A1 | 10/2008 | Ozersky et al. |
| 2009/0020139 A1 | 1/2009 | Sumnicht et al. |
| 2009/0020248 A1 | 1/2009 | Sumnicht et al. |
| 2009/0065164 A1 | 3/2009 | Goto et al. |
| 2009/0084874 A1 | 4/2009 | Alam et al. |
| 2009/0221812 A1 | 9/2009 | Ankerfors et al. |
| 2010/0024998 A1 | 2/2010 | Wildlock et al. |
| 2010/0059191 A1 | 3/2010 | Garcia Melgarejo et al. |
| 2010/0132901 A1 | 6/2010 | Wild |
| 2010/0139527 A1 | 6/2010 | Fernandez-Garcia |
| 2010/0212850 A1 | 8/2010 | Sumnicht et al. |
| 2010/0233468 A1 | 9/2010 | Ioelovich et al. |
| 2010/0272938 A1 | 10/2010 | Mitchell et al. |
| 2010/0272980 A1 | 10/2010 | Kowata et al. |
| 2011/0081554 A1 | 4/2011 | Ankerfors et al. |
| 2011/0088860 A1* | 4/2011 | Heijnesson-Hulten ................. D21H 17/24 162/164.1 |
| 2011/0114765 A1 | 5/2011 | Brady et al. |
| 2011/0186252 A1 | 8/2011 | Subramanian et al. |
| 2011/0223401 A1 | 9/2011 | Harlin et al. |
| 2011/0259537 A1 | 10/2011 | Husband et al. |
| 2011/0274908 A1 | 11/2011 | Kowata et al. |
| 2011/0277947 A1 | 11/2011 | Hua et al. |
| 2012/0043039 A1 | 2/2012 | Paltakari et al. |
| 2012/0094953 A1 | 4/2012 | Gane et al. |
| 2012/0107480 A1 | 5/2012 | Gane et al. |
| 2012/0125547 A1 | 5/2012 | Akai |
| 2012/0132383 A1 | 5/2012 | Laine et al. |
| 2012/0205065 A1 | 8/2012 | Esser |
| 2012/0216718 A1 | 8/2012 | Berglund et al. |
| 2012/0277351 A1 | 11/2012 | Yano et al. |
| 2012/0318471 A1 | 12/2012 | Turkki et al. |
| 2013/0000855 A1 | 1/2013 | Nuopponen et al. |
| 2013/0017349 A1 | 1/2013 | Heiskanen et al. |
| 2013/0053454 A1 | 2/2013 | Heiskanen et al. |
| 2013/0126112 A1 | 5/2013 | Gane et al. |
| 2013/0131193 A1 | 5/2013 | Gane et al. |
| 2013/0133848 A1 | 5/2013 | Heijnesson-Hulten et al. |
| 2013/0180680 A1 | 7/2013 | Axrup et al. |
| 2013/0284387 A1 | 10/2013 | Umemoto et al. |
| 2013/0345416 A1 | 12/2013 | Laukkanen et al. |
| 2014/0058077 A1 | 2/2014 | Laukkanen et al. |
| 2014/0302337 A1 | 10/2014 | Gane et al. |
| 2014/0345816 A1 | 11/2014 | Heiskanen et al. |
| 2014/0370179 A1 | 12/2014 | Gane et al. |
| 2014/0371172 A1 | 12/2014 | Gane et al. |
| 2015/0101769 A1 | 4/2015 | Laine et al. |
| 2015/0101770 A1 | 4/2015 | Laine et al. |
| 2015/0144279 A1 | 5/2015 | Laine et al. |
| 2015/0330024 A1 | 11/2015 | Gane et al. |
| 2016/0273165 A1 | 9/2016 | Laine et al. |
| 2016/0299119 A1 | 10/2016 | Laukkanen et al. |

FOREIGN PATENT DOCUMENTS

| | | |
|---|---|---|
| CA | 1149219 A | 7/1983 |
| CA | 1162819 A | 2/1984 |
| CA | 2292587 A1 | 12/1998 |
| CA | 2093545 C | 3/2001 |
| CA | 2437616 A1 | 2/2005 |
| CA | 2750082 A1 | 8/2010 |
| CH | 648071 A | 2/1985 |
| CN | 85108131 A | 5/1987 |
| CN | 1089675 A | 7/1994 |
| CN | 1173904 A | 2/1998 |
| CN | 1200128 A | 11/1998 |
| CN | 1278830 A | 1/2001 |
| CN | 2437616 Y | 7/2001 |
| CN | 1524145 A | 8/2004 |
| CN | 1585839 A1 | 2/2005 |
| CN | 101360863 A | 2/2005 |
| CN | 1665984 A | 9/2005 |
| CN | 101203644 A | 6/2008 |
| CN | 102869831 B1 | 9/2015 |
| DK | 175143 B1 | 6/2004 |
| EP | 51230 A1 | 5/1982 |
| EP | 39628 B1 | 7/1984 |
| EP | 0198622 A1 | 10/1986 |
| EP | 273745 A2 | 7/1988 |
| EP | 442183 A1 | 8/1991 |
| EP | 492600 A1 | 7/1992 |
| EP | 499578 A1 | 8/1992 |
| EP | 0614948 A1 | 9/1994 |
| EP | 619140 A2 | 10/1994 |
| EP | 0625611 A1 | 11/1994 |
| EP | 0726356 A1 | 8/1996 |
| EP | 579171 B1 | 1/1997 |
| EP | 785307 A2 | 7/1997 |
| EP | 790135 A2 | 8/1997 |
| EP | 0852588 B1 | 7/1998 |
| EP | 619140 B1 | 5/1999 |
| EP | 0935020 A1 | 8/1999 |
| EP | 0949294 A1 | 10/1999 |
| EP | 988322 B1 | 1/2002 |
| EP | 1053213 B1 | 5/2002 |
| EP | 1469126 A1 | 10/2004 |
| EP | 1538257 A1 | 6/2005 |
| EP | 1936032 A1 | 6/2008 |
| EP | 2196579 A1 | 6/2010 |
| EP | 2216345 A1 | 8/2010 |
| EP | 2236545 A1 | 10/2010 |
| EP | 2236545 B1 | 10/2010 |
| EP | 2236664 A1 | 10/2010 |
| EP | 1907626 B1 | 11/2010 |
| EP | 2386682 B1 | 11/2011 |
| EP | 2386683 B1 | 3/2014 |
| EP | 2563967 B1 | 8/2017 |
| EP | 2640893 B1 | 8/2017 |
| ES | 2100781 A1 | 6/1997 |
| FR | 2689530 A1 | 10/1993 |
| FR | 2774702 A1 | 8/1999 |
| GB | 663621 | 12/1951 |
| GB | 2260146 A | 4/1993 |
| GB | 2265916 A | 10/1993 |
| GB | 2275876 A | 9/1994 |
| GB | 2528487 A | 1/2016 |
| JP | 1-156587 A | 6/1989 |
| JP | H04-81813 A | 7/1992 |
| JP | H0598589 A | 4/1993 |
| JP | 6-158585 A | 6/1994 |
| JP | 06-240588 A | 8/1994 |
| JP | 8-81896 A | 3/1996 |
| JP | 2528487 B2 | 8/1996 |

(56) References Cited

FOREIGN PATENT DOCUMENTS

| | | |
|---|---|---|
| JP | 8-284090 A | 10/1996 |
| JP | 9-124702 A | 5/1997 |
| JP | 10158303 A | 6/1998 |
| JP | 10237220 A | 9/1998 |
| JP | 11-269796 A | 10/1999 |
| JP | 2976485 B2 | 11/1999 |
| JP | 2981555 B1 | 11/1999 |
| JP | 2000-170029 A | 6/2000 |
| JP | 3421446 B2 | 6/2003 |
| JP | 2004231796 A | 8/2004 |
| JP | 2004523676 A | 8/2004 |
| JP | 2004-534911 A | 11/2004 |
| JP | 2005505708 A | 2/2005 |
| JP | 2006008857 A | 1/2006 |
| JP | 2007262594 A | 10/2007 |
| JP | 2008007899 A | 1/2008 |
| JP | 2008150719 A | 7/2008 |
| JP | 2008169497 A | 7/2008 |
| JP | 2009161613 A | 7/2009 |
| JP | 2009243014 A | 10/2009 |
| JP | 2009263854 A | 11/2009 |
| JP | 2010168716 A | 8/2010 |
| JP | 2010-202987 A | 9/2010 |
| JP | 2010202987 A | 9/2010 |
| JP | 2012-522145 A | 9/2012 |
| JP | 5666553 B2 | 2/2015 |
| JP | 5894525 B2 | 3/2016 |
| KR | 20080096747 A | 11/2008 |
| NL | 8102857 A | 1/1983 |
| RU | 2208079 C2 | 7/2003 |
| RU | 2345189 C2 | 1/2009 |
| SU | 499366 A1 | 1/1977 |
| TW | 200609278 | 3/2006 |
| TW | 200609278 A | 3/2006 |
| TW | 201013017 A1 | 4/2010 |
| WO | 93001333 A1 | 1/1993 |
| WO | 9315270 A1 | 8/1993 |
| WO | 94/05595 A1 | 3/1994 |
| WO | 9404745 A1 | 3/1994 |
| WO | 97/12917 A1 | 4/1997 |
| WO | 9712917 A1 | 4/1997 |
| WO | 9718897 A2 | 5/1997 |
| WO | 98/28362 A1 | 7/1998 |
| WO | 98/56860 A2 | 12/1998 |
| WO | 9855693 A1 | 12/1998 |
| WO | 9856826 A1 | 12/1998 |
| WO | 9856860 A1 | 12/1998 |
| WO | 9954045 A1 | 10/1999 |
| WO | 0166600 A1 | 9/2001 |
| WO | 0198231 A1 | 12/2001 |
| WO | 02086238 A1 | 10/2002 |
| WO | 02090651 A1 | 11/2002 |
| WO | 02/100955 A1 | 12/2002 |
| WO | 02100955 A1 | 12/2002 |
| WO | 03033815 A2 | 4/2003 |
| WO | 2004/016852 A1 | 2/2004 |
| WO | 2004/055267 A1 | 7/2004 |
| WO | 2005/014934 A2 | 2/2005 |
| WO | 2005061793 A1 | 7/2005 |
| WO | 2005/100489 A1 | 10/2005 |
| WO | 2005/123840 A1 | 12/2005 |
| WO | 2006/009502 A1 | 1/2006 |
| WO | 2006/041401 A1 | 4/2006 |
| WO | 2006/136651 A1 | 12/2006 |
| WO | 2007/006794 A1 | 1/2007 |
| WO | 2007/091942 A1 | 8/2007 |
| WO | 2007/096180 A2 | 8/2007 |
| WO | 2007088974 A1 | 8/2007 |
| WO | 2007/110639 A1 | 10/2007 |
| WO | 2008/008576 A2 | 1/2008 |
| WO | 2008/033283 A1 | 3/2008 |
| WO | 2008/076056 A1 | 6/2008 |
| WO | 2008/076071 A1 | 6/2008 |
| WO | 2008/095764 A1 | 8/2008 |
| WO | 2008132228 A1 | 11/2008 |
| WO | 2009074491 A1 | 6/2009 |
| WO | 2009/123560 A1 | 10/2009 |
| WO | 2009122982 A1 | 10/2009 |
| WO | 2009126106 A1 | 10/2009 |
| WO | 2009153225 A1 | 12/2009 |
| WO | 2010/003860 A2 | 1/2010 |
| WO | 2010015726 A1 | 2/2010 |
| WO | 2010092239 A1 | 8/2010 |
| WO | 2010102802 A1 | 9/2010 |
| WO | 2010112519 | 10/2010 |
| WO | 2010112519 A1 | 10/2010 |
| WO | 2010115785 | 10/2010 |
| WO | 2010115785 A1 | 10/2010 |
| WO | 2010125247 A2 | 11/2010 |
| WO | 2010131016 A2 | 11/2010 |
| WO | 2011004300 A1 | 1/2011 |
| WO | 2011004301 A1 | 1/2011 |
| WO | 2011/042607 A1 | 4/2011 |
| WO | 2011/048000 A1 | 4/2011 |
| WO | 2011/056130 A1 | 5/2011 |
| WO | 2011/059398 A1 | 5/2011 |
| WO | 2011/068457 A1 | 6/2011 |
| WO | 2011064441 A1 | 6/2011 |
| WO | 2011/141876 A1 | 11/2011 |
| WO | 2011/141877 A1 | 11/2011 |
| WO | 2011134938 A1 | 11/2011 |
| WO | 2011134939 A1 | 11/2011 |
| WO | 2011/154335 A1 | 12/2011 |
| WO | 2012/039668 A1 | 3/2012 |
| WO | 2012098296 A2 | 7/2012 |
| WO | 2014091212 A1 | 6/2014 |

OTHER PUBLICATIONS

Dupiont, A.-L., "Cellulose in lithium chloride/N;N-dimethylacetamide, optimisation of a dissolution method using paper substrates and stability of the solutions," Polymer, 2003, 44, 4117-4126.*

Martin Ragnar, et al., "Pulp," Ullmann's Encyclopedia of Industrial Chemistry, published online 2000, 89 pages.*

The Third Party Observations dated Oct. 21, 2011 for European Application No. EP 09156703.2.

The European Search Report dated Jun. 26, 2009 for European Application No. EP 09156703.2.

The Office Action dated Jan. 28, 2014 for Japanese Application No. 2012-502646.

The Examination Report dated Feb. 11, 2014 for Taiwanese Application No. 099109562.

The First Office Action dated Oct. 23, 2013 for Chinese Application No. 201080015263.X.

The Office Action for Russian Application No. 2011143811.

The Office Action for Russian Application No. 2011143854.

The Office Action dated Jan. 7, 2014 for Canadian Application No. 2,755,495.

The Office Action for Ukrainian Application No. a 2011 12682.

Third Party Observations dated Jun. 6, 2012 for European Application No. EP 09156683.6.

Third Party Observations dated Oct. 21, 2011 for European Application No. EP 09156683.6.

European Search Opinion dated Jun. 26, 2009 for European Application No. EP 09156683.6.

Third Party Observations dated Jun. 6, 2012 for European Application No. EP 09156703.2.

Third Party Observations dated May 18, 2011 for European Application No. EP 09156703.2.

Third Party Observations dated Jun. 11, 2012 for European Application No. 10161166.3.

The Communication dated Aug. 6, 2013 for European Application No. EP 11716257.8.

The Response to the Communication dated Nov. 5, 2013 for European Application No. EP 11716257.8.

The International Search Report dated Nov. 3, 2011 for PCT Application No. PCT/EP2011/056540.

The Written Opinion of the International Searching Authority dated Oct. 27, 2012 for PCT Application No. PCT/EP2011/056540.

(56) References Cited

OTHER PUBLICATIONS

Third Party Observations dated Jan. 9, 2012 for European Application No. EP 10161173.9.
Third Party Observations dated Jun. 11, 2012 for European Application No. EP 10161173.9.
Third Party Observations dated Apr. 19, 2013 for European Application No. EP 10161173.9.
Chauhan et al. "Use of Nanotechnology for High Performance Cellulosic and Papermaking Products." 2012, Cellulose Chemistry and Technology, 46(5-6), pp. 389-400.
Charani et al. "Rheological Characterization of High Concentrated MFC Gel from Kenaf Unbleached Pulp." 2013, Cellulose, vol. 20, pp. 727-740.
Opietnik et al. "TENCEL® Gel—A Novel Cellulose Micro Suspension." 2013, Lenzinger Berichte, vol. 91, pp. 89-92.
Shen et al. "Carbohydrate-based fillers and pigments for papermaking: A review" 2011, Carbohydrate Polymers, vol. 85, 17-22.
The International Search Report dated Aug. 17, 2010 for PCT Application No. PCT/EP2010/054233.
The Written Opinion of the International Searching Authority dated Sep. 30, 2011 for PCT Application No. PCT/EP2010/054233.
Third Party Observations dated Jun. 11, 2012 for European Application No. EP 1073884.4.
Third Party Observations dated Feb. 17, 2012 for European Application No. EP 1073884.4.
Third Party Observations dated Jun. 11, 2012 for European Application No. EP 10711423.3.
Third Party Observations dated Feb. 17, 2012 for European Application No. EP 10711423.3.
Third Party Observations dated Feb. 4, 2013 for European Application No. EP 11716257.8.
Third Party Observations dated Feb. 4, 2013 for European Application No. EP 11719499.3.
The Communication dated Jan. 2, 2014 for European Application No. EP 10713884.4.
The Communication dated Feb. 21, 2013 for European Application No. EP 10713884.4.
The Communication dated Jan. 2, 2014 for European Application No. EP 09156683.6.
The Communication dated Jul. 31, 2013 for European Application No. EP 09156683.6.
The Communication dated Feb. 7, 2013 for European Application No. EP 09156683.6.
The Communication dated Jun. 27, 2011 for European Application No. EP 09156683.6.
The Communication dated Jul. 31, 2013 for European Application No. EP 09156703.2.
The Communication dated Feb. 7, 2013 for European Application No. EP 09156703.2.
The Communication dated May 20, 2011 for European Application No. EP 09156703.2.
The Communication dated Mar. 26, 2014 for European Application No. EP 10711423.3.
The Communication dated Sep. 24, 2012 for European Application No. EP 10711423.3.
The Communication dated Mar. 15, 2013 for European Application No. 10161166.3.
The Communication dated Feb. 15, 2013 for European Application No. 11716257.
The Communication dated Mar. 15, 2013 for European Application No. EP 10161173.9.
European Search Report dated Sep. 7, 2010 for European Application No. EP 10161173.9.
The Communication dated Oct. 11, 2013 for European Application No. EP 1179499.
The International Search Report dated Jun. 7, 2010 for PCT Application No. PCT/EP2010/054231.
The Written Opinion for the International Searching Authority dated Jun. 7, 2010 for PCT Application No. PCT/EP2010/054231.
Third Party Observations dated May 27, 2011 for European Application No. 09156683.6.
The Office Action dated Jan. 16, 2013 for Chinese Application No. 201080015262.5.
Little et al. "Hydrated Lime—more than just a filler." National Lime Association.
Sixta, "Handbook of Pulp." Wood Structure and Morphology, vol. 1, pp. 41 and 42.
Hubbe, "Mini-encyclopedia of papermaking wet end chemistry: Fibrillation." NC State University Internet Citation p. 1.
Hubbe et al. "What happens to cellulosic fibers during papermaking and recycling? A Review." BioResources 2(4): pp. 739-788.
Siró et al. "Microbibrillated cellulose and new nanocomposite materials: A Review." Cellulose (2010) 17, pp. 459-494.
De Oliveira et al., "Synthesis and Characterization of Microcrystaliine Cellulose Produced from Bacterial Cellulose," J. Therm. Anal. Caiorim, (2011) 106, pp. 703-709.
Dupont, A.L., "Cellulose in lithium chloride/N, N-dimethylacetamide, optimisation of a dissolution method using paper substrates and stability of the solutions", Polymer 44 (15):4117-4126.
Herrick et al., "Microfibriiated, Cellulose: Morphology and Accessibility," Journal of Applied Polymer Science: Applied Polymer Symposium, (1983) 37, pp. 797-813.
Kumar et al, "Comparison of Nano- and Microfibriiated Cellulose Films," Cellulose, (2014) 21, pp. 3443-3456.
Paakko et al., "Enzymatic Hydrolysis Combined with Mecllanical Shearing and High-Pressure Homogenization for Nanoscale Cellulose Fibrils and Strong Gels." Biomacromolecules, (2007) 8, pp. 1934-1941.
Postek et al., "Production and Applications of Cellulose Nanomaterials," TAPPI Press (2013) Chapter 2, pp. 169-173.
Sofia et al., "A Comparision of Cellulose Nanocrystals and Cellulose Nanofibres Extracted from Bagasse Using Acid and Ball Milling Methods," Adv. Nat Sci.: Nanosci. Nanotechnol., (2016) 7, 9 pages.
Habibi et al., "Cellulose Nanocrystals: Chemistry, Self-Assembly, and Applications," Chem. Rev. (2010) 110, pp. 3479-3500.
Lavoine et al., "Microfibrillated Cellulose—Its Barrier Properties and Applications in Cellulosic Materials: A Review," Carbohydrate Polymers 90 (2012) pp. 735-764.
Samir et al., "Review of Recent Research into Cellulosic Whiskers, Their Properties and Their Application in Nanocomposite Field," Biomacromolecules (2005) 6, pp. 612-626.
Canadian Office Action for corresponding Canadian Patent Application No. 2755493, dated May 28, 2014, 4 pages.
Canadian Office Action for corresponding Canadian Patent Application No. 2755493, dated Feb. 19, 2015, 3 pages.
Chinese Office Action for corresponding Chinese Patent Application No. 201610882363.1; dated Jan. 25, 2018, 19 pages.
European Office Action for corresponding European Patent Application No. 14175471.3 dated Oct. 6, 2017, 3 pages.
Third Party Observations dated Mar. 16, 2015 for European Patent Application No. 14175471.3, 6 pages.
European Extended Search Report for European Patent Application No. 14175471.3 dated Oct. 23, 2014, 8 pages.
Japanese Office Action for corresponding Japanese Patent Application No. 2014-248634 dated Jan. 9, 2018, 11 pages.
Japanese Office Action for corresponding Japanese Patent Application No. 2014-248634 dated Mar. 10, 2017, 6 pages.
Korean Office Action for corresponding Korean Patent Application No. 10-2017-7011268 dated Jun. 21, 2017, 5 pages.
Malaysian Substantive Examination Report for corresponding Malaysian Patent Application No. PI 2014002508 dated Nov. 30, 2017, 4 pages.
Taiwan Examination Report and Search Report for corresponding Taiwan Patent Application No. 099109560 dated Jun. 22, 2015, 12 pages.
Pöhler, Tiina & Lappalainen, Timo & Tammelin, Tekla & Eronen, Paula & Hiekkataipale, Panu & Vehniäinen, Annikki & M. Koskinen, Timo. (2011). "Influence of fibrillation method on the character of nanofibrillated cellulose (NFC)," 2010 TAPPI International Conference on Nanotechnology for the Forest Product Industry, Dipoli Congress Centre, Espoo, Finland, Sep. 27-29, 2010, 22 pages.

(56) References Cited

OTHER PUBLICATIONS

Ahola et al., "Model Films from Native Cellulose Nanofibrils. Preparation, Swelling, and Surface Interactions," Biomacromolecules, 9: 2008 pp. 1273-1282.
Notice of Appeal filed Dec. 21, 2017 for corresponding European Patent No. EP2236664, 1 page.
Provision of the minutes in accordance with Rule 124(4) EPC dated Nov. 2, 2017, of the oral proceedings for corresponding European Patent No. EP2236664, 5 pages.
Third Party Written Submission dated Sep. 25, 2017 for corresponding European Patent No. 2236664, 2 pages.
Summons to Attend Oral Proceedings Pursuant to Rule 115(1) EPC dated Mar. 22, 2017 for corresponding European Patent No. EP2236664, 10 pages.
Decision Revoking European Patent No. 2236664 dated Nov. 2, 2017, 12 pages.
Response dated Mar. 2, 2017 to Communication of Notices of Opposition Pursuant Rule 79(1) EPC for corresponding European Patent No. 2236664, 9 pages.
Optifinder™ DF Deflakers, "Improved quality through effective deflaking." Stock Preparation and Recycled Fiber Systems, Metso Paper, 4 pages, 2006.
http://puu.tkk.fi/em/research/research_group/chemical_pupling_and_wood_refinery/seminar_presentations/43 knuts_100609_laitoksen_sisainen_seminaariesitys.pdf;Knuts, M.SC. Aaro, "Process installation and optimization to D refine and produce NFC materials." pp. 1-9, 2010.
Notice of Opposition against EP 2236664 B1, EP Application No. 09156683.6, dated Sep. 29, 2016 from European Patent Office.
European Office Action dated Sep. 20, 2016 for European Patent Application No. 14 175 451.5, 3 pages.
Third Party Observations dated Mar. 16, 2015 for European Patent Application No. 14 175 451.5, 6 pages.
European Search Report dated Oct. 23, 2014 for European Patent Application No. 14 175 451.5, 6 pages.
Campinhos Jr. "Sustainable Plantations of High-Yield Eucalyptus Trees of Production of Fiber: the Aracruz Case." New Forests (1999) 17: 129-143.
European Notice of Opposition dated Dec. 19, 2014 for European Patent No. EP2386682, 17 pages.
European Office Action of Mar. 10, 2017 for European Patent Application No. 10 713 884.4, 4 pages.
Patt et al., "Paper and Pulp," Ulmann's Encyclopedia of Industrial Chemistry, published online Jun. 2000, 157 pages.
European Office Action from the European Patent Office dated Oct. 11, 2013 for European Patent Application No. 11 719 499.3, 4 pages.
European Third Party Observations dated Apr. 12, 2013 for European Application No. EP 10161166.3, 4 pages.
European Third Party Observations dated Feb. 4, 2013 for European Application No. EP 11716257.8, 8 pages.
European Third Party Observations dated Jan. 9, 2012 for European Application No. EP 10161166.3, 6 pages.
European Third Party Observations dated Oct. 21, 2011 for European Application No. EP 09156703.2, 4 pages.
Japanese Office Action dated Apr. 14, 2015 for Japanese Patent Application No. 2012-502647, 7 pages.
Europe, Office Action dated Mar. 15, 2013 for European Application No. 10161166.3, 4 pages.
Notice of Opposition against EP 2236664 B1, EP Application No. 09156683.6, dated Jul. 18, 2017 from European Patent Office, 10 pages.
Japanese Office Action dated Mar. 31, 2015 for Japanese Patent Application No. 2013-506621, 7 pages.
Korean Office Action dated Aug. 11, 2017 for Korean Patent Application No. 10-2017-7017876, 5 pages.
Optifiner™ DF Deflakers, "Improved quality through effective deflaking." Stock Preparation and Recycled Fiber Systems, Metso Paper, 4 pages.

Indian Examination Report dated Aug. 24, 2017 for Indian Patent Application No. 2046/MUMNP/2011, 7 pages.
Russian Official Action dated Apr. 22, 2015 for Russian Patent Application No. 2015109771, 4 pages.
Somboon, et al. "Grit segments in TMP refining. Part 2: Potential for energy reduction", Appita Journal, vol. 62, No. 1, 2009, pp. 42-45 and 59.
Smook, Handbook for Pulp and Paper Technologies, 1992, Angus Wilde Publications, 2nd Edition, Chap. 13.
Somboon, et al. "Grit segments in TMP refining. Part 1: Operating parameters and pulp quality", Appita Journal, vol. 62 No. 1, 2009, pp. 37-41.
Somboon, Phichit, "On the Application of Grits to Therrnomechanical Pulp Refining." TKK Reports in Forest Products Technology, Series A7, Espoo 2009, 61 pages.
Spence, et al. "The effect of chemical composition on microfibrillar cellulose films from wood pulps: Mechanical processing and and physical properties", BioResource Technology, vol. 101, 2010, pp. 5961-5968.
Syverud, et al. "The influence of microfibrillated cellulose, MFG, on paper strength and surface properties", Paper and Fibre Research Institute and Norwegian University of Science and Technology, pp. 1-32.
Taiwan Examination and Search Report dated May 17, 2016 for Taiwan Patent Application No. 100114616, 11 pages.
Taiwan Examination Report dated Feb. 11, 2014 for Taiwanese Application No. 099109562, 17 pages.
Response to Notice of Opposition Against EP2236664, dated Mar. 2, 2017, submitted to the European Patent Office, 9 pages.
Taniguchi, Takashi, "New Films Produced from Microfibrillated Natural Fibres", Polymer International, vol. 47, 1998, pp. 291-294.
Terao, et al. "Pulp-Filler Interaction (3)—The Influence of Wet Pressing and Cellulosic Fines Addition on the Structure and Properties of Filler Loaded Papers", vol. 8, 1989, pp. 65-73.
Torvinen, et al. "Flexible filler—nanocellulose structures", VTT Technical Research Centre of Finland—1 page.
UK Search Report for UK Application No. GB0908401.3, dated Sep. 14, 2009, 1 page.
Vietnam, First Examination Report dated Dec. 30, 2014 for Vietnamese Patent Application No. 1-2012-03429, 4 pages.
Vietnam, Second Examination Report dated Oct. 8, 2015 for Vietnamese Patent Application No. 1-2012-03429, 5 pages.
Vietnam, Third Examination Report dated Apr. 28, 2016 for Vietnamese Patent Application No. 1-2012-03429, 2 pages.
Waterhouse, J .F., "Whither Refining?", Institute of Paper Science and Technology, No. 649, 1997, 40 pages.
Zhao, et al., "Ultrasonic technique for extracting nanofibers from nature materials" Applied Physics Letters 90, Jul. 31, 2012, 2007, 2 pages.
Zirconium Oxide Data sheet, downloaded online from www.stanfordmaterials.com, downloaded on Jan. 12, 2012, 7 pages.
Zirconium, Silicate Data sheet, downloaded online from www.reade.com, downloaded on Jan. 12, 2012, 2 pages.
Zou, et al. "Production of Nanocrystalline Cellulose and its Potential Applications in Specialty Papers." Pira Specialty Papers Conference, Nov. 2010, pp. 1-30.
Zou, et al. "Review of Microfibrillated Cellulose (MFG) for Papermaking", Pulp and Paper Engineering, School of Chemical and Biomolecular Eng., Georgia Institute of Technology, 10 pages.
Korean Office Action dated Jul. 28, 2016 for Korean Patent Application No. 10-2011-7025315, 7 pages.
Russian Office Action dated Jan. 21, 2014 for Russian Patent Application No. 2011143854, 7 pages.
Taiwan Reasons for Rejection dated Nov. 7, 2014 for Taiwanese Application No. 099109562, 7 pages.
Taiwan Reasons for Rejection dated Apr. 26, 2017 for Taiwanese Application No. 099109562, 5 pages.
Abe, et al. "Obtaining Cellulose Nanofibers with a Uniform Width of 15 nm from Wood", Bio macromolecules, vol. 8, (2007) pp. 3276-3278.
Ahola, Susanna, "Properties and Interfacial Behavior of Cellulose Nano fibrils." Doctoral Thesis, 2008, 82 pages.

(56) References Cited

OTHER PUBLICATIONS

Ankerfors, et al. "Nano Cellulose Developments in Scandinavia", Paper and Coating Chemistry Symposium (PCCS), Jun. 2009, Hamilton, Canada, 43 pages.
Ankerfors, Mikael, "The manufacture of micro fibrillated cellulose (MFG) its applications." Nanostructured cellulose and new cellulose derivatives seminar, Nov. 2006, pp. 1-40.
Atrex G-Series, Megatrex, "Technology for Reject Treatment and Recovery." 2 pages.
Australian Patent Examination Report No. 1 dated Feb. 26, 2014 for Australian Patent Application No. 2013202515, 3 pages.
Australian Patent Examination Report dated Jul. 26, 2012 for Australian Patent Application No. 2010247184, 6 pages.
Australian Patent Examination Report No. 1 dated May 14, 2013 for Australian Patent Application No. 2011246521, 2 pages.
Australian Patent Examination Report No. 1, dated Sep. 16, 2015 for Australian Patent Application No. 2014227494, 3 pages.
Australian Examination Report dated May 3, 2013 for Australian Patent Application No. 2011246522, 4 pages.
Berglund et al., "Nanostructured Cellulose Products." Finnish-Swedish Wood Material Science Research Programme Opening Seminar, 2004, Helsinki, Finland, 28 pages.
Bhatnagar et al., "Processing of Cellulose Nanofiber-reinforced Composites." Journal of Reinforced Plastics and Composites, vol. 24, No. 12, 2005, pp. 1259-1268.
Canadian Office Action dated Apr. 28, 2016 for Canadian Patent Application No. 2,796,132, 3 pages.
Canadian Office Action dated May 11, 2015 for Canadian Patent Application No. 2,755,495, 4 pages.
Canadian Office Action dated Sep. 2, 2015 for Canadian Patent Application No. 2,796,132, 3 pages.
Ducheyne, Paul et al., eds "Comprehensive Biomaterials," vol. 1. Newnes, 2015, p. 409.
Canadian Office Action dated Dec. 18, 2013 for Canadian Application No. 2,748,137, 2 pages.
Canadian Office Action dated Apr. 26, 2016 for Canadian Patent Application No. 2, 796, 135, 4 pages.
Canadian Office Action dated Sep. 3, 2015 for Canadian Patent Application No. 2, 796, 135, 3 pages.
Characterisation Newsletter "Micro fibrillated Cellulose", No. 5, Jan. 2009, pp. 1-2.
Chinga-Carrasco, "Cellulose fibres, nanofibrils and microfibrils: The morphological sequence of MFC components from a plant physiology and fibre technology point of view." Chinga-Carrasco Nanoscale Research Letters 2011, vol. 6:417, 8 pages.
Chinese Fifth Office Action dated Feb. 15, 2016 for Chinese Patent Application No. 201080015263.X, 7 pages.
Chinese First Notification of Office Action for Chinese Patent Application No. 201510628033.5, dated Jan. 10, 2017, 17 pages.
Chinese First Office Action dated May 6, 2014 for Chinese Patent Application No. 201180020949.2, 14 pages.
Third Party Observations dated Jun. 11, 2012 for European Patent Application No. 10161173.9, 3 pages.
Chinese Fourth Office Action dated Oct. 13, 2015 for Chinese Patent Application No. 201080015263.X, 10 pages.
Chinese Office Action dated Jan. 6, 2014 for Chinese Application No. 201080003690.6, 15 pages.
Chinese Second Office Action dated Jun. 11, 2014 for Chinese Patent Application No. 201080015263.X, 14 pages.
Chinese Second Office Action dated Mar. 4, 2015 for Chinese Patent Application No. 201180020949.2, 5 pages.
Chinese Third Office Action dated Feb. 27, 2015 for Chinese Patent Application No. 201080015263.X, 23 pages.
Chinese Office Action dated Apr. 10, 2015 for Chinese Patent Application No. 201180020953.9, 5 pages.
Chinese Office Action dated Jan. 13, 2015 forChinese Patent Application No. 201180020953.9, 12 pages.
Chinese Office Action dated May 22, 2014 for Chinese Patent Application No. 201180020953.9, 20 pages.

Chinga-Carrasco, et al. "Computer-assisted quantification of the Iti-scale structure of films made of nanofibrillate cellulose." J. Nanopart Res. 2010, pp. 841-851.
Peng et al., "Drying cellulose nanofibrils: in search of a suitable method." Published online: Dec. 2, 2011, Cellulose, DOI 10.1007/s10570-011-9630-z, 12 pages.
Herrick et al. "Microfibrillated Cellulose: Morphology and Accessibility," Journal of Applied Polymer Science, Applied Polymer Symposium 37—Proceedings of the Ninth Cellulose Conference II. Symposium on Cellulose and Wood as Future Chemical Feedstocks and Sources of Energy, and General Papers, John Wiley & Sons, Inc., May 24-27, 1982, 11 pages.
European Communication dated Aug. 6, 2013 for European Patent Application No. 11716257.8, 4 pages.
Eichhorn et al., "Review: current international research into cellulose nanofibres and nanocomposites." Journal of Materials Science, vol. 45, No. 1, 2010, pp. 1-33.
Eriksen et al., "The use of microfibrillated cellulose produced from kraft pulp as strength enhancer in TMP paper." Nordic Pulp and Paper Research Journal, vol. W. No. 3, 2008, p. 299-304.
Response to the Communication dated Nov. 5, 2013 for European Patent Application No. 11716257.8, 11 pages.
European Communication dated May 2, 2016 for European Patent Application No. 10 713 884.4, 3 pages.
European Examination Report dated Oct. 27, 2015 for European Patent Application No. 14 175 471.3, 3 pages.
European Examination Report dated Oct. 27, 2015 for European Patent Application No. 14 175 451.5, 3 pages.
European Examination Report dated Sep. 16, 2016 for European Patent Application No. 14 175 471.3, 4 pages.
European Extended European Search Report dated Jan. 15, 2013, for European Patent Application No. 12189681.5, 5 pages.
European Communication dated Sep. 24, 2012 for European Patent Application No. 10711423.3, 10 pages.
The Office Action dated Jan. 28, 2014 for U.S. Appl. No. 13/138,647, 18 pages.
Subramanian et al., "Calcium Carbonate—Cellulose Fibre Composites; the Role of Pulp Refining," Paper Technology, Dec. 2006 Pulp Refining, pp. 27-31.
Falini et al., "Oriented Crystallization of Vaterite in Collagenous Matrices," Chem. Eur. J. (1998) 4:1048-1052.
Champinhos Jr. "Sustainable Plantations of High-Yield Eucalyptus Trees of Production of Fiber: the Aracruz Case." New Forests (1999) 17: 129-143.
Auad et al., "Charactizeration of Nanocellulose-Reinforced Shape Memory Polyurethanes." Polymer International (2008) 57: 651-659. Online Publication Date: Dec. 13, 2007.
Kenny et al., "Lime and Limestone," Ulmann's Encyclopedia of Industrial Chemistry (2012) 21: 37-69.
International Search Report and Written Opinion for International Application No. PCT/EP2011/056542, dated May 27, 2011, 9 pages.
Third Party Observations dated Jun. 6, 2012 for European Patent Application No. 09156683.6, 4 pages.
Third Party Observations dated Oct. 21, 2011 for European Patent Application No. 09156683.6, 4 pages.
Third Party Observations dated Jun. 6, 2012 for European Patent Application No. 09156703.2, 4 pages.
Third Party Observations dated May 18, 2011 for European Patent Application No. 09156703.2, 6 pages.
Third Party Observations dated Apr. 19, 2013 for European Patent Application No. 10161173.9, 5 pages.
Third Party Observations dated May 27, 2011 for European Patent Application No. 09156683.6, 7 pages.
European Office Action dated Feb. 6, 2014 for related European Application No. 12 189 681.5-1308, 3 pages.
European Office Action dated Mar. 7, 2014, for European Application No. 10 727 476.3-1308, 5 pages.
European Office Action dated May 26, 2014, for European Application No. 10 727 476.3-1308, 4 pages.
European Office Action dated Nov. 30, 2012 for European Application No. 10 727 476.3-2124, 4 pages.

(56) References Cited

OTHER PUBLICATIONS

European Office Action dated Oct. 25, 2013 for European Application No. 10 727 476.3-1308, 3 pages.
European Office Action dated May 2, 2016 for European Patent Application No. 10 713 884.4, 3 pages.
European Partial European Search Report of European Application No. 16163032, Jul. 26, 2016, 3 pages.
European Search Report dated Jun. 26, 2009 for European Application No. 09156703.2, 7 pages.
European Search Report dated Sep. 8, 2010 for European Application No. 10161166.3.
European Office Action dated Mar. 29, 2016 for European Patent Application No. 11719499.3, 3 pages.
Japanese Office Action dated Nov. 7, 2017 for Japanese Patent Application No. 2016-234040, 11 pages.
European Third Party Observation dated Jun. 6, 2012 for European Application No. 09156703.2, 4 pages.
International Preliminary Report on Patentability dated Oct. 30, 2012 for PCT/EP2011/056542, 6 pages.
European Third Party Observations dated Apr. 12, 2013 for European Application No. EP 10161173.9, 4 pages.
European Third Party Observations dated Feb. 17, 2012 for European Application No. EP 10713884.4, 6 pages.
European Third Party Observations dated Feb. 4, 2013 for European Application No. EP 11719499.3, 8 pages.
Iwamoto, et al. "Nano-fibrillation of pulp fibers for the processing of transparent nanocomposites", Applied Physics A, vol. 89, 2007, pp. 461-466.
European Third Party Observations dated May 18, 2011 for European Application No. 09156683.6, 6 pages.
European Third Party Observations dated Oct. 21, 2011 for European Application No. 091566683.6, 4 pages.
European Third Party Observations pursuant to Article 115(1)EPC concerning European Patent Application No. 12 189 581.5, dated Jul. 10, 2014, 15 pages.
European Third Party Observations pursuant to Article 115(1)EPC concerning European Patent Application No. 10727476.3, dated Jul. 22, 2014, 18 pgs.
European Office Action from the European Patent Office dated Mar. 15, 2013 for European Patent Application No. 10 161 166.3, 4 pages.
Innventia, "Processes for Nano cellulose," http://www.innventia.com/templates/STFIPage_9108.aspx, 2011, 1 page.
European Office Action from the European Patent Office dated Aug. 6, 2013 for European Patent Application No. 111716257.8, 4 pages.
Siqueira et al., "Cellulosic Bionanocomposites: A Review of Preparation, Properties and Applications," Polymers (2010) 2, pp. 728-765, doi: 10.3390/polym2040728.
Fukui, Yoshitaka, "Microfibrillated Cellulose", vol. 60, No. 24, 1985, pp. 5-12.
GL&V, The Atrex System at M-real Hallein Paper Mill in Austria, "Atrex is running well and us money!" 4 pages.
Henriksson, "Cellulose Nanofibril Networks and Composites", KTH Chemical Science and Engineering, 2008, 60 pages.
Hentze, Hans-Peter, "From Nano cellulose Science towards Applications", VTT—Technical Research Center of Finland, PulpPaper 2010, Jun. 2010, Helsinki, pp. 1-24.
International Search Report and Written Opinion dated Jun. 22, 2011 for International Application No. PCT/EP2011/056540, 11 pages.
http://puu.tkk.fl/em/research/research_groups/chemical_pupling_and_wood_refinery/seminar_presentations/knuts_100609_laitoksen_sisainen_seminaariesitys.pdf;Knuts, M. SC. Aaro, "Process installation and optimization to refine and produce NFC materials." pp. 1-9.
India, Examination Report dated Jun. 12, 2017 for Indian Patent Application No. 1474/MUMNP/2011.
Indonesian Examination Report dated Oct. 13, 2015 for Indonesian Patent Application No. W00201103474, 4 pages.
Indonesian Office Action dated Mar. 10, 2016 for Indonesian Patent Application No. W00201103469, 2 pages.
Indonesian Office Action dated Apr. 18, 2017 for Indonesian Patent Application No. WO 00 2012 04369, 4 pages.
Klemm et al., "Cellulose: Fascinating Biopolymer and Sustainable Raw Material." Angew Chem. Int Ed. 2005 vol. 44, pp. 3358-3393.
Peltola, Maarit, "Preparation of Microfibrillated Cellulose" Master of Science Thesis, Tampere University of Technology, May 2009, 98 pages.
Henriksson, et al. "Cellulose Nanopaper Structures of High Toughness", Biomacromolecules, vol. 9, 2008, pp. 1579-1585.
U.S. Notice of Allowance dated Apr. 24, 2018 for U.S. Appl. No. 14/808,480, 8 pages.
U.S. Non-Final Office Action dated Jun. 14, 2018 for U.S. Appl. No. 14/474,749, 8 pages.
U.S. Notice of Allowance dated May 22, 2017 for U.S. Appl. No. 13/640,533, 6 pages.
Indian Examination Report dated Jun. 29, 2018 for Indian Patent Application No. 2424/MUMNP/2012, 5 pages.
European Office Action for corresponding European Patent Application No. 14175471.3 dated May 17, 2018, 3 pages.
Response by Opponent to Notice of Appeal Against EP2236664, dated Jul. 3, 2018, submitted to the European Patent Office, 15 pages.
"Paper Coating Pigments," TAPPI Monograph Series No. 30, 1966, pp. 34-35.
Chinese Office Action for corresponding Chinese Patent Application No. 201610882363.1, dated Jan. 25, 2018, 27 pages.
Office Action dated Nov. 18, 2015 for U.S. Appl. No. 13/640,513.
The Office Action dated Jan. 27, 2014 for U.S. Appl. No. 13/138,646, 14 pages.
Crofton et al., "Dielectric Studies of Cellulose and Its Derivatives: 1. Acetylation of Cellulose," Polymer (1982) 23:1605-1608.
Daiyong et al., "Advances in Cellulose Chemistry," J. of Chemical Industry and Engineering, vol. 57, No. 8, (2006), pp. 1782-1791.
Daiyong, Ye, "Preparation of Nanocellulose," Progress in Chemistry, vol. 19, No. 10, (2007), pp. 1568-1575.
Esau, Katherine, "Chapter 4, Cell Wall," Anatomy of Seed Plants, 2nd Edition, (1977) pp. 43-48.
European Notice of Opposition dated Dec. 19, 2014 for European Patent No. EP2386683, 15 pages.
European Search Report for European Patent Application No. 17188196.4, dated Nov. 17, 2017, 6 pages.
European Third Party Observations dated Jan. 9, 2012 for European Application No. EP 10161173.9, 6 pages.
European Third Party Observations pursuant to Article 115(1 )EPC concerning European Patent Application No. 12 189 681.5, dated Jul. 10, 2014, 15 pages.
European Search Search Report dated Jun. 26, 2009 for European Application No. EP 09156683.6, 9 pages.
European Search Report for European Patent Application No. 17190151.5, dated Mar. 19, 2018, 5 pages.
European Search Report for European Patent Application No. 18152927.2, dated May 7, 2018, 6 pages.
European Office Action for European Patent Application No. 10713884.4, dated Apr. 19, 2018, 4 pages.
Fahn, A., "Plant Anatomy Fourth Edition," (1990) pp. 32-39.
Fengel et al., "Chapter 4. Cellulose," Wood Chemistry, Ultrastructure, Reactions, (1983) pp. 66-105.
Fengel, D., "Ideas on the Ultrastructure Organization of the Cell Wall Components," J. Polymer Sci.: Part C, No. 36 (1971) pp. 383-392.
Frey-Wyssling and Mühlethaler, "The Fine Structure of Cellulose." Fortschritte der Chemie Organischer Naturstoffe (1951) pp. 1-27.
Hamann, Lutzm Papiertechnische Stiftung, SUNPAP Workshop May 10, 2011, Seventh Framework Programme, 24 pages.
Hubbe et al. "Mini-encyclopedia of papermaking wet-end chemistry." NC State University Internet Citation, Aug. 17, 2010, p. 1.
Hubbe et al., "What happens to cellulosic fibers during papermaking and recycling" A Review. Bioresources 2(4), (2007) 739-788.
Hult et al., "Cellulose Fibril Aggregation—An Inherent Property of Kraft Pulps," Polymer 42 (2001) pp. 3309-3314.

(56) References Cited

OTHER PUBLICATIONS

Indian Examination Report dated Jun. 6, 2018 for Indian Patent Application No. 2018/MUMNP/2011, 6 pages.
Indian Examination Report dated Jun. 12, 2018 for Indian Patent Application No. 2404/MUMNP/2012, 6 pages.
Indonesian Office Action dated Feb. 13, 2018 for Indonesian Patent Application No. W00201204368, 4 pages.
International Report on Patentability for International Patent Application No. PCT/EP2010/054233, dated Oct. 4, 2011, 9 pages.
International Report on Patentability for International Patent Application No. PCT/EP2011/056540, dated Oct. 30, 2012, 6 pages.
International Preliminary Report on Patentability and the Written Opinion dated Oct. 4, 2011 from PCT Patent No. PCT/EP2010/054231, 8 pages.
International Search Report and Written Opinion dated Sep. 3, 2010 for International Application No. PCT/EP2010/054233, 12 pages.
Iwamoto, et al. "Optically transparent composites reinforced with plant fiber-based nanofibers", Applied Physics A, vol. 81, 2005, pp. 1109-1112.
Japanese Official Action dated May 22, 2018 for Japanese Patent Application No. 2016-234040, 4 pages.
Ling-ling and Xiao-quan, "Research Status of the Nano-Crystalline Cellulose," J. of Cellulose Science and Technology, vol. 16, No. 2, (2008), pp. 73-78.
McGinnis and Shafizadeh, "Chapter 1 Cellulose and Hemicellulose," Pulp and Paper: Chemistry and Chemical Technology, (1980) pp. 1-38.
McGraw-Hill, "Cell Walls (Plant)," Encyclopedia of Science and Technology, 5th edition, (1982), pp. 737-741.
New Zealand Office Action for New Zealand Patent Application No. 603756 dated Jun. 20, 2013, 2 pages.
Non-Final Office Action dated Nov. 10, 2014 for U.S. Appl. No. 13/640,513, 12 pages.
"Packaging Technical Manual," Edited by Japan Packaging Technology Association (1994), 12 pages.
Roberts, J.C., "Chapter 2, The Material of Paper," The Chemistry of Paper, RSC Paperbacks, 1996, pp. 11-25.
Roberts, J.C., "Chapter 4, The Material of Paper," The Chemistry of Paper, RSC Paperbacks, 1996, pp. 52-68.
Rowland and Roberts, "The Nature of Accessible Surfaces in the Microstructure of Cotton Cellulose," Journal of Polymer Science: Part A-1, vol. 10, (1972) pp. 2447-2461.
Russian Office Action from Russian Patent Application No. 2011143854 filed on Mar. 10, 2010.
Russian Office Action dated Apr. 22, 2015 for Russian Patent Application No. 2012150441, 7 pages.
Russian Search Report dated Apr. 25, 2018 for Russian Patent Application No. 2014130594, 4 pages.
Saito et al., "Cellulose Nanofibers Prepared by TEMPO-Mediated Oxidation of Native Cellulose," Biomacromolecules, (2007) 8:2485-2491.
Selder, H.; Mannes, W., and Matzke, W., "Broke systems for LWC, MWC and HWC Papers", Voith Sulzer Paper Technology, 8 pages, Dec. 2011.
Singapore Office Action for Singapore Patent Application No. 2012075610, dated Dec. 31, 2014, 21 pages.
Singapore Search and Examination Report for Singapore Patent Application No. 2012075610, dated Nov. 4, 2015, 16 pages.
Statement of Grounds of Appeal for European Patent No. 2236664 dated Mar. 12, 2018, 13 pages.
Syverud and Stenius, "Strength and Barrier Properties of MFC Films," Cellulose 16:75-85 (2009).
Taiwan, Office Action for related Taiwanese Application No. 099115704, dated Jul. 14, 2014.
Taiwan Office Action for Taiwanese Application No. 1-2012-03429, dated Dec. 30, 2014, 4 pages.
Taiwan Office Action for Taiwanese Application No. 1-2012-03429, dated Oct. 8, 2015, 3 pages.
Taiwan Office Action for Taiwanese Application No. 1-2012-03429, dated Apr. 28, 2016, 2 pages.
Taiwanese Office Action and Search Report for Taiwanese Patent Application No. 104124236 dated Feb. 26, 2018, 10 pages.
U.S. Final Office Action dated Jan. 12, 2017 for U.S. Appl. No. 13/640,513, 10 pages.
U.S. Final Office Action dated Jan. 28, 2014 for U.S. Appl. No. 13/138,647, 18 pages.
U.S. Final Office Action dated Jul. 20, 2017 for U.S. Appl. No. 14/474,749, 12 pages.
U.S. Final Office Action dated Mar. 26, 2014 for U.S. Appl. No. 13/640,513, 14 pages.
U.S. Final Office Action dated May 8, 2013 for U.S. Appl. No. 13/138,646, 11 pages.
U.S. Final Office Action dated May 9, 2013 for U.S. Appl. No. 13/138,647, 15 pages.
U.S. Final Office Action dated May 9, 2016 for U.S. Appl. No. 14/474,749, 10 pages.
U.S. Final Office Action dated Nov. 18, 2015 for U.S. Appl. No. 13/640,513, 8 pages.
U.S. Issue Fee Payment dated Sep. 17, 2014 for U.S. Appl. No. 13/138,646, 5 pages.
U.S. Issue Notification dated Oct. 28, 2014 for U.S. Appl. No. 13/138,647, 1 page.
U.S. Issue Notification dated Oct. 8, 2014 for U.S. Appl. No. 13/138,646, 1 page.
U.S. Non-Final Office Action dated Dec. 19, 2016 for U.S. Appl. No. 14/474,749, 12 pages.
U.S. Non-Final Office Action dated Dec. 28, 2017 for U.S. Appl. No. 13/640,513, 9 pages.
U.S. Non-Final Office Action dated Dec. 3, 2015 for U.S. Appl. No. 14/474,749, 11 pages.
U.S. Non-Final Office Action dated Jan. 15, 2013 for U.S. Appl. No. 13/138,646, 16 pages.
U.S. Non-Final Office Action dated Jan. 22, 2013 for U.S. Appl. No. 13/138,647, 19 pages.
U.S. Non-Final Office Action dated Mar. 11, 2016 for U.S. Appl. No. 13/640,513, 8 pages.
U.S. Non-Final Office Action dated May 15, 2015 for U.S. Appl. No. 13/640,513, 13 pages.
U.S. Non-Final Office Action dated Sep. 11, 2013 for U.S. Appl. No. 13/138,646, 13 pages.
U.S. Non-Final Office Action dated Sep. 11, 2013 for U.S. Appl. No. 13/138,647, 17 pages.
U.S. Non-Final Office Action dated Sep. 6, 2013 for U.S. Appl. No. 13/640,513, 13 pages.
U.S. Notice of Allowance dated Feb. 23, 2018 for U.S. Appl. No. 14/474,749, 9 pages.
U.S. Notice of Allowance dated May 23, 2014 for U.S. Appl. No. 13/138,647, 8 pages.
U.S. Notice of Allowance dated May 27, 2014 for U.S. Appl. No. 13/138,646, 8 pages.
U.S. Notice of Allowance dated Sep. 16, 2014 for U.S. Appl. No. 13/138,646, 7 pages.
U.S. Notice of Allowance dated Sep. 5, 2014 for U.S. Appl. No. 13/138,647, 7 pages.
U.S. Issue Fee Payment dated Sep. 11, 2014 for U.S. Appl. No. 13/138,647, 5 pages.
U.S. Notice of Allowance dated Dec. 22, 2017 for U.S. Appl. No. 14/808,480, 8 pages.
U.S. Non-Final Office Action dated May 19, 2017 for U.S. Appl. No. 14/808,480, 6 pages.
U.S. Final Office Action dated Nov. 28, 2016 for U.S. Appl. No. 14/808,480, 8 pages.
U.S. Non-Final Office Action dated May 2, 2016 for U.S. Appl. No. 14/808,480, 15 pages.
U.S. Non-Final Office Action dated Oct. 21, 2015 for U.S. Appl. No. 14/808,480, 11 pages.
U.S. Notice of Allowance dated Dec. 21, 2017 for U.S. Appl. No. 13/640,533, 7 pages.
U.S. Non-Final Office Action dated Sep. 1, 2017 for U.S. Appl. No. 13/640,533, 8 pages.
U.S. Final Office Action dated Nov. 28, 2016 for U.S. Appl. No. 13/640,533, 8 pages.

(56) References Cited

OTHER PUBLICATIONS

U.S. Non-Final Office Action dated Mar. 24, 2016 for U.S. Appl. No. 13/640,533, 12 pages.
U.S. Notice of Allowance dated Nov. 25, 2015 for U.S. Appl. No. 13/640,533, 8 pages.
U.S. Notice of Allowance dated Aug. 20, 2015 for U.S. Appl. No. 13/640,533, 6 pages.
U.S. Notice of Allowance dated Jan. 20, 2015 for U.S. Appl. No. 13/640,533, 5 pages.
U.S. Notice of Allowance dated Dec. 2, 2014 for U.S. Appl. No. 13/640,533, 8 pages.
U.S. Non-Final Office Action dated Apr. 25, 2014 for U.S. Appl. No. 13/640,533, 15 pages.
U.S. Final Office Action dated Dec. 19, 2014 for U.S. Appl. No. 13/640,533, 8 pages.
U.S. Non-Final Office Action dated Jun. 14, 2013 for U.S. Appl. No. 13/640,533, 15 pages.
U.S. Notice of Allowance dated May 11, 2018 for U.S. Appl. No. 13/640,533, 7 pages.
Janardhnan, et al. "Isolation of Cellulose Microfibrils—An Enzymatic Approach", BioResources, vol. 1, No. 2, 2006, pp. 176-188.
Japanese Notice of Rejection dated Mar. 31, 2015 for Japanese Patent Application No. 2013-506620, 9 pages.
Indonesia, Examination Report dated Oct. 13, 2015 for Indonesia Patent Application No. W00201103474, 4 pages.
Japanese Office Action dated Apr. 15, 2014 for Japananese Patent No. 2012-502647, 12 pages.
Japanese Office Action dated Dec. 8, 2015 for Japanese Patent Application No. 2014-248634, 8 pages.
Notice of Opposition dated Dec. 19, 2014 for European Patent No. EP238682, 22 pages.
Japanese Office Action dated Nov. 29, 2016 for Japanese Patent Application No. 2015-159928, 11 pages.
Japanese Office Action dated Oct. 20, 2015 for Japanese Patent No. 2012-502647, 3 pages.
Japanese Official Action dated Oct. 27, 2015 for Japanese Patent Application No. 2013-506620, 4 pages.
Japanese Office Action dated Dec. 1, 2015 for Japanese Patent Application No. 2013-506621, 5 pages.
Japanese Office Action dated Mar. 31, 2015 for Japanese Patent Application No. 2013-506621, 8 pages.
Kang, Taegeun, "Role of External Fibrillation in Pulp and Paper Properties," Doctoral Thesis, Helsinki University of Technology, Laboratory of Paper and Printing Technology Reports, Series A28, Espoo 2007, 50 pages.
Klemm, et al. "Nanocelluloses as Innovative Polymers in Research and Application", Adv. Polymer Science, vol. 205, 2006, pp. 49-96.
Klungness, et al. "Fiber-Loading: A Progress Report", TAPPI Proceedings, 1994 Recycling Symposium, pp. 283-290.
Korean Notice of Rejection for Korean Patent Application No. 10-2015-7030983 dated Jul. 29, 2016, 16 pages.
Korean Office Action dated Feb. 20, 2017 for Korean Patent Application No. 10-2016-7030178, 7 pages.
Korean Office Action dated Jan. 27, 2016 for Korean Patent Application No. 10-2011-7025315, 13 pages.
Korean Office Action dated Jul. 29, 2016 for Korean Patent Application No. 10-2012-7030744, 11 pages.
Korea, Office Action dated Mar. 28, 2016 for Korean Patent Application No. 10-2011-7025318, 12 pages.
Korean Office Action dated Jul. 29, 2016 for Korean Patent Application No. 10-2012-7030761, 13 pages.
Littiunen, Kuisma, "Free radical graft copolymerization of microfibrillated cellulose", Master's Thesis, Helsinki University of Technology, Sep. 2009, 83 pages.
Ioelovich and Figovsky, "Structure and Properties of Nanoparticles Used in Paper Compositions", Mechanics of Composite Materials, vol. 46, No. 4, 2010, pp. 435-442.
Ioelovich, Michael, "Cellulose as a Nanostructured Polymer: A Short Review." BioResources, vol. 3, No. 4, 2008, pp. 1403-1418.

Luukkanen, Lauri, "Reducing of Paper Porosity and Roughness Through Layered Structure", Aalto University School of Science and Technology, Master's thesis for the degree of Master of Science in Technology, Espoo, May 2010, 132 pages.
Malaysian Examination Report dated Nov. 30, 2015 for Malaysian Patent Application No. PI 2011004631, 3 pages.
Malaysian Examination Report dated Oct. 15, 2015 for Malaysian Patent Application No. PI 2012004747, 3 pages.
Mathur, V. "GRI's Fibrous Filler Technology Presentation to TAPPI", Philadelphia, PA (slides only), 2005, pp. 1-10.
Mill (grinding) http://en_wikipedia.org/w/index.php?title-File:Hammer_mill_open-_front_full.jgp, 8 pgs.
Mori, et al. "Effect of cellulose nano-fiber on calcium carbonate crystal form", Polymer Preprints, Japan, vol. 56, No. 2, 2007—1 page.
Morseburg, et al. "Assessing the combined benefits of clay and nanofibrillated cellulose in layered TMP-based sheets", Cellulose, No. 5, vol. 16, 2009, pp. 795-806.
Mullite, 2001 [downloaded online Dec. 6, 2016], Minerals Data Publishing.
Nakagaito, et al. "The effect of fiber content on the mechanical and thermal expansion properties of bio composites based on microfibrillated cellulose", Cellulose, vol. 15, 2008, pp. 459-494.
OPTIFINER™ DF Deflakers, "Improved quality through effective deflaking." Stock Preparation and Recycled Fiber Systems, Metso Paper, 2006, 4 pages.
Pinkney et al., "Microfibrillated Cellulose—A New Structural Material." Engineering Doctorate Conference (2012), Unviersity of Birminghamm 2 pgs.
Pohler et al. "Influence of fibrillation method on the character of nanofibrillated cellulose (NFC)." The Finnish Centre of Nanocellulosic Technologies, 22 pages.
Porubska, et al. "Homo- and heteroflocculation of papermaking fines and fillers", Colloids and Surfaces A: Physiochem. Eng. Aspects, Elsevier Science, vol. 210, 2002, pp. 223-230.
Subramanian, "Engineering Fine Paper by Utilizing the Structural Elements of the Raw Materials," TKK Reports in Department of Forest Products Technology, Series A1 ESPOO 2008, pp. 1-66.
Product information for the Ultra-fine Friction Grinder "Supermasscolloider," 1 page, retrieved from http:www.masuko.com/English/product/Masscolloder.html (2014).
European Office Action dated Jun. 27, 2011 for European Application No. 09156683.6, 7 pages.
Russian Application No. 2011143854, (abstract) for EP No. 2236545A1.
Saito, et al. "Homogeneous Suspensions of Individualized Microfibrils from TEMPO-Catalyzed Oxidation of Native Cellulose," Biomacromolecules, American Chemical Society, vol. 7, No. 6, 2006, pp. 1687-1691.
Selder, et al. "Broke systems for LWC, MWC and HWC Papers", Voith Sulzer Paper Technology, 7 pages.
Silenius, Petri, "Improving the Combinations of Critical Properties and Process Parameters of Printing and Writing Papers and Paperboards by New Paper-Filling Methods", Helsinki University of Technology Laboratory of Paper Technology Reports, Series A 14, Espoo 2002, 168 pages.
Sinnott et al. "Slurry Flow in a Tower Mill", Seventh International Conference on CFO in the Minerals and Process Industries, CSIRO, Melbourne, Australia, Dec. 9-11, 2009, pp. 1-7.
Taiwan Examination and Search Report dated Apr. 29, 2016 for Taiwan Patent Application No. 100114616, 11 pages.
Yano, Hiroyuki, High Performance of Bio Fibers by the Addition of Filler, vol. 55, Machine No. 4, 2009, pp. 63-68.
Canadian Office Action for Canadian Patent Application No. 2755495 dated May 11, 2015, 4 pages.
Chinese Office Action for Chinese Patent Application No. 201080015262.5 dated Jul. 9, 2013, 6 pages.
Notice of Opposition to European Patent No. 2236545 dated May 27, 2015, 19 pages.
Korean Office Action and Notice Requesting Consultation, dated Nov. 25, 2016 for Korean Patent Application No. 10-2011-7025315, 10 pages.
Brazilian Examination Report for Brazilian Patent Application No. PI1013180-9, dated Oct. 16, 2018, 6 pages.

(56) References Cited

OTHER PUBLICATIONS

Chinese Second Office Action dated Sep. 12, 2018 for Chinese Patent Application No. 201610882363.1, 6 pages.
Opponent Submission Preparation Oral Proceedings Against EP2236664, dated Nov. 13, 2018, 5 pages.
U.S. Final Office Action for U.S. Appl. No. 13/640,513, dated Oct. 10, 2018, 9 pages.
U.S. Non-Final Office Action for U.S. Appl. No. 16/040,652, dated Nov. 13, 2018, 15 pages.
European Office Action for European Patent Application No. 14175471.3, dated Oct. 15, 2018, 4 pages.

* cited by examiner

PROCESS FOR THE PRODUCTION OF NANO-FIBRILLAR CELLULOSE SUSPENSIONS

CROSS-REFERENCE TO RELATED APPLICATIONS

This is a continuation of U.S. application Ser. No. 13/138,647, filed Oct. 14, 2011, now U.S. Pat. No. 8,871,057, which is a U.S. national phase of PCT Application No. PCT/EP2010/054231, filed Mar. 30, 2010, which claims priority to European Application No. EP 09156683.6, filed Mar. 30, 2009 and U.S. Provisional Application No. 61/212,108, filed Apr. 6, 2009, the contents of which are hereby incorporated by reference.

The present invention relates to a process for producing nano-fibrillar cellulose suspensions and the nano-fibrillar cellulose obtained by this process.

Cellulose is the structural component of the primary cell wall of green plants and is the most common organic compound on Earth. It is of high interest in many applications and industries.

Cellulose is the major constituent of paper and cardboard and of textiles made from cotton, linen, and other plant fibres. Cellulose can be converted into cellophane, a thin transparent film, and into rayon, an important fibre that has been used for textiles since the beginning of the 20th century. Both cellophane and rayon are known as "regenerated cellulose fibres".

Cellulose fibres are also used in liquid filtration, to create a filter bed of inert material. Cellulose is further used to make hydrophilic and highly absorbent sponges.

For industrial use, cellulose is mainly obtained from wood pulp and cotton. It is mainly used to produce cardboard and paper; and to a smaller extent it is converted into a wide variety of derivative products.

Cellulose pulp as a raw material is processed out of wood or stems of plants such as hemp, linen and manila. Pulp fibres are built up mainly from cellulose and other organic components (hemicellulose and lignin). The cellulose macromolecules (composed of 1-4 glycosidic linked β-D-Glucose molecules) are linked together by hydrogen bonds to form a so called primary fibril (micelle) which has crystalline and amorphous domains. Several primary fibrils (around 55) form a so called microfibril. Around 250 of these microfibrils form a fibril.

The fibrils are arranged in different layers (which can contain lignin and/or hemicellulose) to form a fibre. The individual fibres are bound together by lignin as well.

The pulps used in papermaking are often obtained by grinding the wood and an optional processing by heat and chemistry to remove undesired compounds from the cellulosic fibres.

The fibres are ground and cut to a certain fineness (depending on the desired properties). The grinding of the fibres is achieved with a refiner (such as a conic rotor-stator mill or disc- or double-disc refiners). The refiner also fibrillates the fibres on the surface which means that some fibrils are partially pulled out of the surface of the fibre. This leads to a better retention of, and, frequently, a better adhesion to, pigments which may be added in paper production, and also to an enhanced potential of hydrogen bonding between the fibres of the paper. This results in improved mechanical properties. A side-effect is also that the paper becomes denser and more transparent because of a loss of light scattering as the size of the scattering centres moves away from the accepted optimum of half the wave length of light (glassine and greaseproof papers).

When fibres become refined under applied energy they become fibrillated as the cell walls are broken and torn into attached strips, i.e. into fibrils. If this breakage is continued to separate the fibrils from the body of the fibre, it releases the fibrils. The breakdown of fibres into microfibrils is referred to as "micro fibrillation". This process may be continued until there are no fibres left and only fibrils of nano size (thickness) remain.

If the process goes further and breaks these fibrils down into smaller and smaller fibrils, they eventually become cellulose fragments. The breakdown to primary fibrils may be referred to as "nano-fibrillation", where there may be a smooth transition between the two regimes.

The achievable fineness with conventional refiners however is limited. Also, a number of other apparati for breaking down particles are not capable of breaking down cellulose fibres to nano-fibrils, such as fluffers mentioned in US 2001/0045264, which are only capable of separating given size fractions of fibres from each other.

Similarly, in WO 02/090651 a method for recycling pulp rejects generated during manufacturing of paper, paperboard or cardboard is described, wherein cleaner rejects containing among other things fibres, pigments and/or fibres are milled to a certain grain size by ball mills. However, no mention is made of the fibrillation of the fibres present, let alone the fibrillation into nano-fibrils.

If a further breakdown of the fibres into nano-fibrils is desired other methods are needed.

For example, in U.S. Pat. No. 4,374,702 a process for preparing microfibrillated cellulose is described comprising passing a liquid suspension of fibrous cellulose through a high pressure homogenizer having a small diameter orifice in which the suspension is subjected to a pressure drop of at least 3000 psi and a high velocity shearing action followed by a high velocity decelerating impact against a solid surface, repeating the passage of said suspension through the orifice until said cellulose suspension becomes a substantially stable suspension, said process converting said cellulose into microfibrillated cellulose without substantial chemical change of the cellulose starting material.

U.S. Pat. No. 6,183,596 B1 discloses a process for producing super microfibrillated cellulose by passing a slurry of a previously beaten pulp through a rubbing apparatus having two or more grinders which are arranged so that they can be rubbed together to microfibrillate the pulp to obtain microfibrillated cellulose and further super microfibrillate the obtained microfibrillated cellulose with a high-pressure homogenizer to obtain the super microfibrillated cellulose.

Furthermore, ultra-fine friction grinders can be used, wherein the grinder reduces the fibres into fines by mechanical shearing (cf. e.g. U.S. Pat. No. 6,214,163 B1).

There are a number of problems regarding the fibrillation of cellulose fibres, which have to be overcome.

For example, the mechanical production of nano-fibrillar cellulose often has the problem of an increasing viscosity during the fibrillation process. This can stop the process completely or increase the needed specific energy.

The efficiency of the breakdown processes often is rather low, and there is a considerable amount of fibres just cut, but not fibrillated into fibrils.

Therefore, there is a continuous need for providing more efficient processes for producing nano-fibrillar cellulose suspensions, and it is one objective of the present invention to provide a new and efficient process for the production of nano-fibrillar cellulose suspensions.

It has been found that the addition and co-processing of certain fillers and/or pigments with cellulose fibre containing pulp may have a positive influence on the fibrillating process in many respects, as described in more detail below.

Thus, the process of the present invention is characterized by the following steps:
 (a) providing cellulose fibres;
 (b) providing at least one filler and/or pigment;
 (c) combining the cellulose fibres and the at least one filler and/or pigment;
 (d) fibrillating the cellulose fibres in the presence of the at least one filler and/or pigment.

Nano-fibrillar cellulose in the context of the present invention means fibres, which are at least partially broken down to primary fibrils.

In this respect, fibrillating in the context of the present invention means any process which predominantly breaks down the fibres and fibrils along their long axis resulting in the decrease of the diameter of the fibres and fibrils, respectively.

Cellulose fibres, which can be used in the process of the present invention may be such contained in pulps selected from the group comprising *eucalyptus* pulp, spruce pulp, pine pulp, beech pulp, hemp pulp, cotton pulp, and mixtures thereof. In this respect, the use of kraft pulp, especially bleached long fibre kraft pulp may be especially preferred. In one embodiment, all or part of this cellulose fibre may be issued from a step of recycling a material comprising cellulose fibres. Thus, the pulp may also be recycled pulp.

The size of the cellulose fibres in principle is not critical. Useful in the present invention generally are any fibres commercially available and processable in the device used for their fibrillation. Depending on their origin, cellulose fibres may have a length of from 50 mm to 0.1 µm. Such fibres, as well as such having a length of preferably 20 mm to 0.5 µm, more preferably from 10 mm to 1 mm, and typically from 2 to 5 mm, can be advantageously used in the present invention, wherein also longer and shorter fibres may be useful.

It is advantageous for the use in the present invention that the cellulose fibres are provided in the form of a suspension, especially an aqueous suspension. Preferably such suspensions have a solids content of from 0.2 to 35 wt-%, more preferably 0.25 to 10 wt-%, especially 1 to 5 wt-%, and most preferably 2 to 4.5 wt-%, e.g. 1.3 wt-% or 3.5 wt-%.

The at least one filler and/or pigment is selected from the group comprising precipitated calcium carbonate (PCC); natural ground calcium carbonate (GCC); dolomite; talc; bentonite; clay; magnesite; satin white; sepiolite, huntite, diatomite; silicates; and mixtures thereof. Precipitated calcium carbonate, which may have vateritic, calcitic or aragonitic crystal structure, and/or natural ground calcium carbonate, which may be selected from marble, limestone and/or chalk, are especially preferred. In a special embodiment, the use of ultrafine discrete prismatic, scalenohedral or rhombohedral precipitated calcium carbonate may be advantageous.

The fillers and/or pigments can be provided in the form of a powder, although they are preferably added in the form of a suspension, such as an aqueous suspension. In this case, the solids content of the suspension is not critical as long as it is a pumpable liquid.

In a preferred embodiment, the filler and/or pigment particles have a median particle size of from 0.5 to 15 µm, preferably 0.7 to 10 µm, more preferably 1 to 5 µm and most preferably 1.1 to 2 µm.

Especially preferably, the filler and/or pigment particles have a median particle size of from 0.03 to 15 µm, preferably 0.1 to 10 µm, more preferably 0.2 to 5 µm and most preferably 0.2 to 4 µm, e.g. 1.5 µm or 3.2 µm.

For the determination of the weight median particle size, $d_{50}$, for particles having a $d_{50}$ greater than 0.5 µm, a Sedigraph 5100 device from the company Micromeritics, USA was used. The measurement was performed in an aqueous solution of 0.1 wt-% $Na_4P_2O_7$. The samples were dispersed using a high-speed stirrer and ultrasound. For the determination of the volume median particle size for particles having a $d_{50} \leq 500$, a Malvern Zetasizer Nano ZS from the company Malvern, UK was used. The measurement was performed in an aqueous solution of 0.1 wt % $Na_4P_2O_7$. The samples were dispersed using a high-speed stirrer and ultrasound.

The fillers and/or pigments may be associated with dispersing agents such as those selected from the group comprising homopolymers or copolymers of polycarboxylic acids and/or their salts or derivatives such as esters based on, e.g. acrylic acid, methacrylic acid, maleic acid, fumaric acid, itaconic acid, e.g. acryl amide or acrylic esters such as methylmethacrylate, or mixtures thereof alkali polyphosphates, phosphonic-, citric- and tartaric acids and the salts or esters thereof or mixtures thereof.

The combination of fibres and at least one filler and/or pigment can be carried out by adding the filler and/or pigment to the fibres in one or several steps. As well, the fibres can be added to the filler and/or pigment in one or several steps. The filler and/or pigment as well as the fibres can be added entirely or in portions before or during the fibrillating step. However, the addition before fibrillating is preferred.

During the fibrillation process, the size of the fillers and/or pigments as well as the size of the fibres can change.

In one embodiment before fibrillating the pH of the combination of cellulose fibres and at least one filler and/or pigment is adjusted to a pH of 10 to 12, e.g. 11.

This adjustment to alkaline pH can be done via addition of preferably milk of lime $(Ca(OH)_2)$ or any other base. After co-processing, the pH in the suspension might then have to be adjusted again to about 7.5 to 9.5, e.g. 8.5.

Generally, the pH of the suspension comprising the combination of fibres and pigment and/or filler should not be less than 6.

It might also be necessary to stabilize the pH, e.g. upon addition of PCC to a fibre suspension, which might lead to an increase of the pH, and a drop of the °SR. In this case the pH may be re-adjusted by commonly used acids or buffers in order to avoid the drop of the Schopper Riegler degree due to the influence of a pH increase.

Furthermore, in one embodiment, the combination is stored for 2 to 12 hours, preferably 3 to 10 hours, more preferably 4 to 8 hours, e.g. 6 hours, prior to fibrillating it, as this ideally results in swelling of the fibres facilitating the fibrillation and thus leads to a faster increase of freeness (°SR) and lower specific refining energy consumption for the same °SR freeness.

Fibre swelling may be facilitated by storage at increased pH, as well as by addition of cellulose solvents like, e.g. copper(II)ethylenediamine, iron-sodium-tartrate or lithium-chlorine/dimethylacetamide, or by any other method known in the art.

Preferably, the weight ratio of fibres to fillers and/or pigments on a dry weight basis is from 1:10 to 10:1, more preferably 1:6 to 6:1, typically 1:4 to 4:1, especially 1:3 to 3:1, and most preferably 1:2 to 2:1, e.g. 1:1.

For example, in one especially preferred embodiment 70 wt-% of bleached longfibre kraft pulp is fibrillated in the presence 30 wt-% ultrafine discrete prismatic (or rhombohedral) PCC, relating to the total dry weight of pulp and PCC, respectively.

One indication of cellulose fibrillation according to the present invention is the increase of the Schopper Riegler degree (°SR).

The Schopper-Riegler degree (°SR) is a measure of the rate at which a diluted pulp suspension may be de-watered and is specified according to the Zellcheming Merkblatt V/7/61 and standardized in ISO 5267/1.

The value is determined by smoothly dispersing the pulp in water and putting it into a drainage chamber where a sealing cone is closed. The sealing cone is lifted pneumatically from the drainage chamber, and, depending on the condition of the fibre suspension, the water flows more or less quickly from the drainage chamber through a side outlet into a measuring cylinder. The water is measured in the cylinder, wherein 10 ml water correspond to 1°SR, and the higher the Schopper-Riegler value, the finer the fibres.

For measuring the Schopper Riegler degree any devices suitable therefore can be used, such as the "Automatic Freeness Tester" supplied by Rycobel, Belgium.

Preferably the combination is fibrillated until the Schopper Riegler degree is increased by ≥4°SR, particularly ≥6°SR, more preferably ≥8°SR, most preferably ≥10°SR, especially ≥15°SR.

In a preferred embodiment the combination of fibres and filler and/or pigment is fibrillated until a final Schopper-Riegler degree of the resulting suspension of ≥30°SR, preferably ≥45°SR, more preferably ≥50°SR, particularly ≥60°SR, e.g. ≥70°SR, especially ≥80°SR is reached.

In a special embodiment, it is however preferred that the final Schopper Riegler degree is ≤95°SR.

The starting Schopper-Riegler degree may be from about 5 to about 90°SR, preferably it is ≤10°SR, preferably ≤25°SR, more preferably ≤40°SR, e.g. ≤60 or ≤75°SR. It may also be greater than 80°SR, if the Δ °SR resulting by the fibrillating step is ≥4°SR.

Looking at the Schopper Riegler degree, it has also been found that the process according to the present invention is much more efficient than fibrillating fibre suspensions in the absence of pigments and/or fillers.

This can be seen by an increased °SR per passage. In order to optimize the fibrillation, the fibre suspension is usually processed by subjecting it to several passages through the fibrillation device.

In this respect, it can be observed that according to the process of the present invention, the °SR per passage is markedly higher than with fibre suspensions only.

This effect can be immediately observed and occurs until a certain number of passages, when no further increase of the °SR is achieved any more.

Thus, in a special embodiment, the change in Schopper Riegler degree per passage is higher for the process of the present invention than for fibre suspensions fibrillated in the absence of pigment and/or filler, until no further essential increase can be observed in both cases.

Also, it can be observed that the simple addition of pigment and/or filler to an already fibrillated system does not in itself lead to as great an increase in the Schopper Riegler degrees as observed when fibrillating in the presence of pigment and/or filler.

Fibrillating is carried out by means of any device useful therefore, as mentioned above. Preferably the device is selected from the group comprising ultra-fine friction grinders such as a Super Mass Colloider, refiners, and homogenizers. In the case of fibrillating in a homogenizer and also in an ultra fine friction grinder, the temperature of the suspension in the homogenizer is preferably above 60° C., more preferably above 80° C. and even more preferably above 90° C.

Another aspect of the present invention is the suspension of nano-fibrillar cellulose obtained by the processes according to the invention.

Furthermore, an aspect of the invention is the advantageous use of the suspension of nano-fibrillar cellulose obtained by the processes according to the invention in paper manufacturing and/or paper finishing.

The nano-fibrillar cellulose suspensions according to the present invention can improve paper strength and may allow for an increase in filler load in uncoated freesheet papers.

Due to their mechanical strength properties the nano-fibrillar cellulose however is also advantageously used in applications such as in material composites, plastics, paints, rubber, concrete, ceramics, adhesives, food, or in wound-healing applications.

The figures described below and the examples and experiments serve to illustrate the present invention and should not restrict it in any way.

EXAMPLES

1. Increase of °SR/Passage Using GCC

Figure 1:
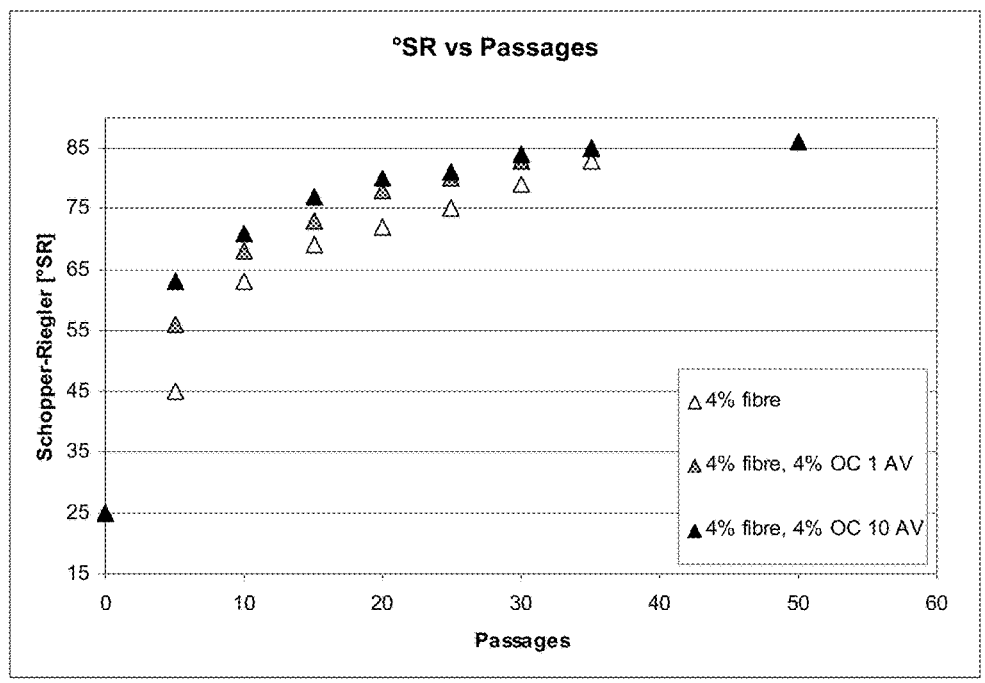
FIG. 1 shows the °SR/passage for pulp suspensions fibrillated with and without different natural ground calcium carbonates.

For examining the development of the °SR/passage, *eucalyptus* pulp with a °SR of 25 was treated first in an ultra-fine friction grinder at 4 wt-% solids content with and without the addition of GCC. A similar experiment was run on an homogenizer with *eucalyptus* pulp at 1.5 wt-% solids content with and without GCC.

Material

GCC: Omyacarb 1-AV (solids content 100 wt % based on weight of fibres present) available from Omya AG. The weight median particle size $d_{50}=1.7$ μm measured by Sedigraph 5100.

Omyacarb 10-AV (solids content 100 wt-% based on weight of fibres present) available from Omya AG. The weight median particle size $d_{50}$ is 10.0 μm measured by Sedigraph 5100.

Pulp: *Eucalyptus* pulp with 25°SR and an equivalent aqueous suspension pH of 7.6.

Example 1—Ultrafine Friction Grinder

For the comparative example *eucalyptus* pulp in the form of dry mats of 500 g per mat (700×1000×1.5 mm) was used. 170 g pulp thereof was torn into pieces of 40×40 mm. 3830 g tap water was added. The suspension was stirred in a 10 dm³ bucket at 2000 rpm using a dissolver disk with a diameter of 70 mm. The suspension was stirred for at least 15 minutes at 2000 rpm.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 µm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1.

For the inventive example *eucalyptus* pulp in the form of dry mats of 500 g per mat (700×1000×1.5 mm) was used. 170 g pulp thereof was torn into pieces of 40×40 mm. 160 g Omyacarb 1-AV was added. 3 830 g tap water was added. The suspension was stirred in a 10 dm³ bucket at 2000 rpm using a dissolver disk with a diameter of 70 mm. The suspension was stirred for at least 15 minutes at 2000 rpm. The suspension had a pH of about 7.5.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 µm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

For the inventive example *eucalyptus* pulp in the form of dry mats of 500 g per mat (700×1000×1.5 mm) was used. 170 g pulp thereof was torn into pieces of 40×40 mm. 160 g Omyacarb 10-AV was added. 3 830 g tap water was added. The suspension was stirred in a 10 dm³ bucket at 2 000 rpm using a dissolver disk with a diameter of 70 mm. The suspension was stirred for at least 15 minutes at 2 000 rpm. The suspension had a pH of about 7.2.

The suspension was then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 µm). The gap between the grinding stones was chosen to be the dynamic 0-point as described in the manual delivered by the supplier. The speed of the rotating grinder was adjusted to be 1200 rpm. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

Results

FIG. 1 shows the development of the °SR as a function of passages through the Supermasscolloider. It becomes apparent that the addition of GCC increases the efficiency of the device per passage.

Example 2—Homogenizer

For the comparative example *eucalyptus* pulp in the form of dry mats of 500 g per mat (700×1000×1.5 mm) was used. 47 g pulp thereof was torn into pieces of 40×40 mm. 2953 g tap water was added. The suspension was stirred in a 5 dm³ bucket at 2000 rpm using a dissolver disk with a diameter of 70 mm. The suspension was stirred for at least 15 minutes at 2000 rpm.

This suspension was fed into the Homogenizer (GEA Niro Soavi NS2006L) but did not run through the machine.

For the inventive example *eucalyptus* pulp in the form of dry mats of 500 g per mat (700×1000×1.5 mm) was used. 47 g pulp thereof was torn into pieces of 40×40 mm. 45 g Omyacarb 1-AV was added. 2953 g tap water was added. The suspension was stirred in a 5 dm³ bucket at 2000 rpm using a dissolver disk with a diameter of 70 mm. The suspension was stirred for at least 15 minutes at 2000 rpm.

This suspension was fed into the Homogenizer (GEA Niro Soavi NS2006L). The flow through the homogenizer was between 100 and 200 g min$^{-1}$ and the pressure was adjusted to be between 200 and 400 bar. The suspension was recirculated several times and samples were taken. The Schopper-Riegler degree (°SR) was measured according to the Zellcheming Merkblatt V/7/61 and standardized in ISO 5267/1. The additional filler was not considered for the requested 2 g/l pulp consistency for the measurement.

Results

The comparative sample that contained no GCC could not be fed through the homogenizer. Only the GCC containing sample showed a good runnability. Schopper-Riegler values are reported in Table 1 after 5 and 10 passages through the homogenizer.

TABLE 1

| Passages | °SR |
|---|---|
| 0 | 25 |
| 5 | 74 |
| 10 | 91 |

2. Increase of °SR Using PCC in a Refiner

Example 3—Ultrafine PCC

Material

PCC: Ultrafine prismatic PCC. The weight median particle size $d_{50}$=1.14 µm measured by Sedigraph 5100 (100 wt-% of particles have a diameter <2 µm; 27 wt-% of particles have a diameter <1 um).
  This PCC was provided in the form of an aqueous suspension having a solids content of 7.9 wt-%.
Pulp: Longfibre bleached kraft pulp with 16°SR and an equivalent aqueous suspension pH of between 6 and 8.
  An aqueous suspension was formed of the above carbonate and pulp such that this suspension had a solids content of approximately 4 wt-% and a carbonate:pulp weight ratio of 29:71.
  Approximately 12.5 dm³ of this suspension were circulated during a period of 9 minutes through an Escher Wyss R 1 L Labor-Refiner under 5.4 kW.
  A Schopper-Riegler (°SR) of the obtained suspension of 92°SR was measured according to the Zellcheming Merkblatt V/7/61 and standardized in ISO 5267/1.

Example 4—Coarse PCC a) Suspension According to the Invention

Material

PCC: Scalenohedral PCC. The weight median particle size $d_{50}$=3.27 µm measured by Sedigraph 5100 (11 wt-% of particles have a diameter <2 µm; 4 wt-% of particles have a diameter <1 um). This PCC was provided in the form of an aqueous suspension having a solids content of 15.8%.

Pulp: *Eucalyptus* with 38°SR and an equivalent aqueous suspension pH of between 6 and 8.

An aqueous suspension was formed of the above carbonate and pulp such that this suspension had a solids content of approximately 9.8 wt-% and a carbonate:pulp weight ratio of 75:25. This suspension presented an 18°SR.

Approximately 38 m³ of this suspension was circulated during a period of 17.5 hours through a Metso Refiner RF-0 under 92 kW at a flow rate of 63 m³/hour.

A Schopper-Riegler (°SR) of the obtained suspension of 73°SR was measured according to the Zellcheming Merkblatt V/7/61 and standardized in ISO 5267/1.

b) Comparative Suspension
Material
PCC: Scalenohedral PCC. The weight median particle size $d_{50}$=3.27 µm measured by Sedigraph 5100 (11 wt-% of particles have a diameter <2 µm; 4 wt-% of particles have a diameter <1 um). This PCC was provided in the form of an aqueous suspension having a solids content of 15.8%.

Pulp: *Eucalyptus* with 38°SR and an equivalent aqueous suspension pH of between 6 and 8.

An aqueous suspension was formed of the above pulp such that this suspension had a solids content of approximately 4.5 wt-%.

Approximately 20 m³ of this suspension was circulated during a period of 17.5 hours through a Metso Refiner RF-0 under 92 kW at a flow rate of 63 m³/hour.

A Schopper-Riegler (°SR) of the obtained suspension of 65°SR was measured according to the Zellcheming Merkblatt V/7/61 and standardized in ISO 5267/1.

To this suspension, the above scalenohedral PCC was added in an amount so as to obtain a carbonate:pulp weight ratio of 75:25. A Schopper-Riegler (°SR) of the obtained suspension of 25°SR was measured according to the Zellcheming Merkblatt V/7/61 and standardized in ISO 5267/1.

This clearly shows that the presence of calcium carbonate during the fibrillation step is essential for obtaining a high Schopper Riegler degree, i.e. an efficient fibrillation of the cellulose fibres.

3. Increase of °SR/Passage Using Different Fillers or Pigments and/or Different Pulps For examining the development of the °SR/passage, *eucalyptus* or pine pulp was treated in an ultra-fine friction grinder with the addition of the filler or pigment as indicated here below.

Material
GCC: Aqueous suspension of natural ground calcium carbonate dispersed with polymeric acrylic acid-based dispersant, solids content 50 wt-%). The volume median particle size $d_{50}$ is 246 nm measured by Malvern Zetasizer Nano ZS.
Talc: Finntalc F40 available from Mondo Minerals.
Pulp: *Eucalyptus* pulp in the form of dry mats, with 17 to 20°SR, a brightness of 88.77% (ISO 2470-2) and an equivalent aqueous suspension pH of between 7 and 8.
Pine pulp in the form of dry mats, with 17 to 20°SR, a brightness of 88.19% (ISO 2470-2) and an equivalent aqueous suspension pH of between 7 and 8.

Example 5—Ultrafine Friction Grinder

In the following examples, the pulp indicated in the Table below, in the form of dry mats, was used. 90 g pulp thereof was torn into pieces of 40×40 mm. The filler indicated in the Table below was added in the indicated amount, along with 2190 g of tap water. The suspensions were each stirred in a 10 dm³ bucket at 2000 rpm using a dissolver disk with a diameter of 70 mm. The suspensions were each stirred for at least 10 minutes at 2000 rpm.

The suspensions were then fibrillated with an ultra-fine friction grinder (Supermasscolloider from Masuko Sangyo Co. Ltd, Japan (Model MKCA 6-2)). The grinding stones were silicon carbide with a grit class of 46 (grit size 297-420 µm). Prior to commencing the following tests, the gap between the grinding stones was set to be the dynamic 0-point as described in the manual delivered by the supplier. For each the tests below, the gap between the grinding stones were further closed from this 0-point by 5 increments, corresponding to an adjustment of −50 µm, as soon as the first material passed between the stones. The speed of the rotating grinder was adjusted to be 2000 rpm for the first 5 passages, and decreased to 1500 rpm for passage 6 and to 1000 rpm for passage 7. Following each passage, the rpm of the friction grinder was increased to approximately 2600 rpm for a period of 5 seconds in order to ensure that a maximum of materials was extracted from the friction grinder before commencing the following passage directly thereafter. The Schopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for Tests a and b at 2 g/l.

|  | Test | |
|---|---|---|
|  | a) | b) |
| Type pulp: | Eucalyptus | Pine |
| Type filler/pigment | GCC | Finntalc F40 |
| Amount filler/pigment (g dry, [g suspension]) | 90 g [180 g] | 90 g |
| Weight ratio filler/pigment:fibre | 1:1 | 1:1 |

Figure 2:
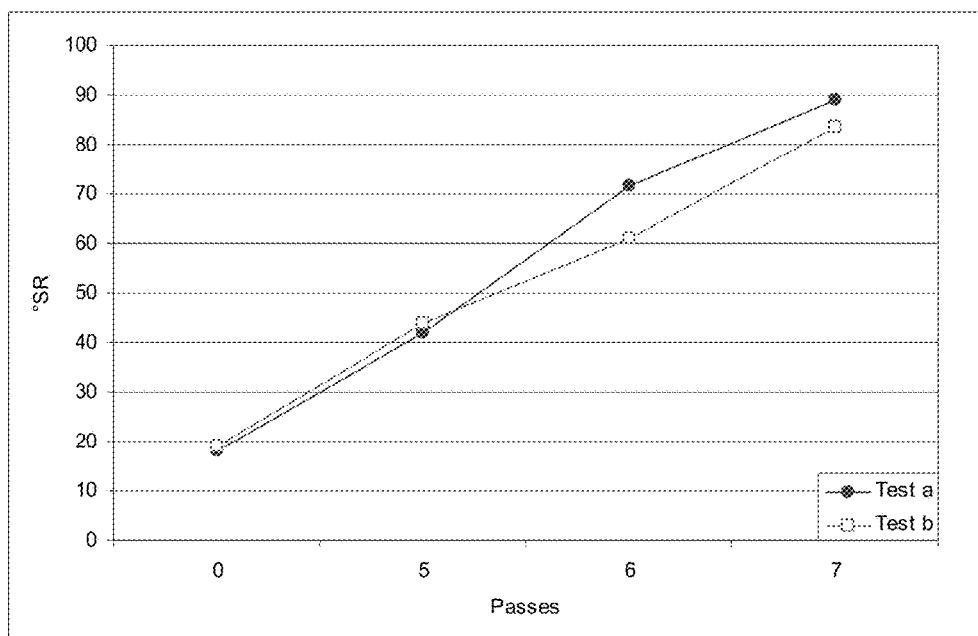
FIG. 2 shows the °SR/passage for pulp suspensions fibrillated with different fillers/pigments.

Results
FIG. 2 shows the development of the °SR as a function of passages through the Supermasscolloider. It becomes apparent that the addition of filler results in an efficient °SR development in the device per passage (compared to tests g and f below), also for other pulp types than *Eucalyptus* and other filler types than GCC and PCC.

4. Increase of °SR/Passage of Comparative Example Treating Pulp in a Ball Mill with and without GCC For examining the development of the °SR/passage, *eucalyptus* pulp was treated in a ball mill with and without the addition of the filler or pigment as indicated here below.

Material
GCC: Omyacarb 1-AV in the form of a powder, available from Omya AG. The weight median particle size $d_{50}$=1.7 µm measured by Sedigraph 5100.
Pulp: *Eucalyptus* pulp in the form of dry mats, with 17 to 20°SR, a brightness of 88.77% (ISO 2470-2) and an equivalent aqueous suspension pH of between 7 and 8.

Example 6—Ball Mill

In the following examples, the pulp indicated in the table below, in the form of dry mats, was used. 88 g pulp thereof was torn into pieces of 40×40 mm. Omyacarb 1-AV was added in the amount indicated in the Table below, along with 5000 g of tap water. The suspensions were each stirred in a 10 dm$^3$ bucket at 2000 rpm using a dissolver disk with a diameter of 70 mm. The suspensions were each stirred for at least 10 minutes at 2000 rpm.

1600 g of each suspension was then introduced in a 3 dm$^3$ porcelain vessel filled with 3500 g of Verac beads having a bead diameter of 2 cm. The vessel was closed and rotated 43 rpm for a period of 24 hours. The Schopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for Tests c and d at 2 g/l.

|  | Test | |
| --- | --- | --- |
|  | c) | d) |
| Type pulp | Eucalyptus | Eucalyptus |
| Type filler/pigment | None | Omyacarb 1-AV |
| Amount filler/pigment (g dry, [g suspension]) | 0 g | 28.2 g |
| Weight ratio filler/pigment:fibre | n/a | 1:1 |

Results

Figure 3:
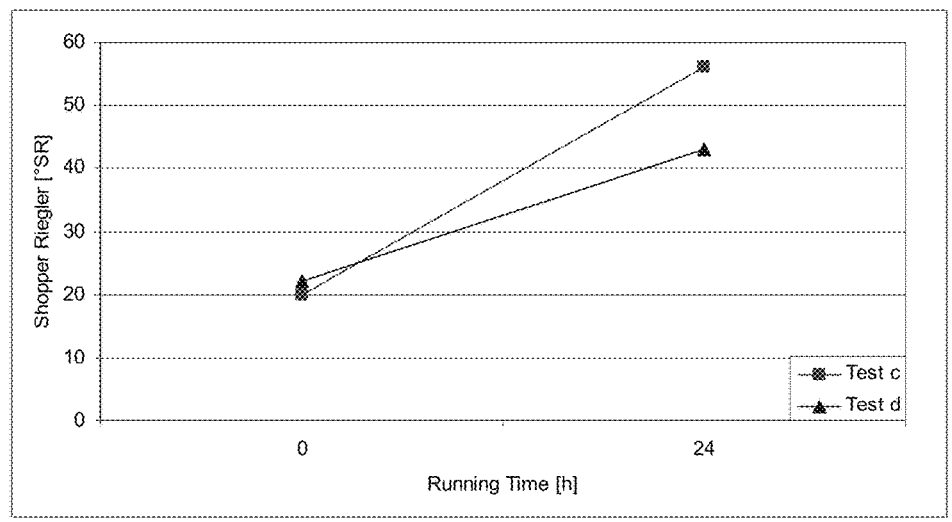
FIG. 3 shows the °SR/running time for pulp suspensions ground in a ball mill with and without natural ground calcium carbonate.

FIG. 3 shows the development of the °SR as a function of passages through the ball mill. It is apparent that the addition of filler does not positively influence the °SR development in the device over time.

5. Beneficial Effect of Filler

Example 7—Ultrafine Friction Grinder

Tests e to g were processed with an ultra-fine friction grinder (Supermasscolloider from Masuko Sangyo Co. Ltd, Japan (Model MKCA 6-2) with mounted silicon carbide stones having a grit class of 46 (grit size 297-420 μm). The gap between the stones was adjusted to "−50" μm (dynamic 0-point, as described in the manual delivered by the supplier). The speed of the rotating grinder was set to 2000 rpm for passes 1-5, to 1500 rpm for pass 6 and to 1000 rpm for pass 7. Samples for Shopper-Riegler degree measurements were taken before grinding, after passes 5, 6 and 7. The Shopper-Riegler degree (°SR) was measured according to the Zellcheming Merkblatt V/7/61 and standardized in ISO 5267/1. The additional filler was not considered for the requested 2 g/l pulp consistency for the measurement. So the pulp consistency was constant for all tests e to g at 2 g/l.

Material:

Omyacarb 1 AV Omyacarb 1-AV available from Omya AG; Fine calcium carbonate powder, manufactured from a high purity, white marble; The weight median particle size $d_{50}$ is 1.7 μm measured by Sedigraph 5100.

*Eucalyptus* pulp Dry mat, brightness: 88.77% (ISO 2470-2), equivalent pulp suspension pH between 7 and 8 and °SR between 17 and 20

Test e):

90 g dry *Eucalyptus* pulp, 2910 g tap water and 90 g Omyacarb 1 AV (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. Samples were taken and measured as described above in the according paragraph.

Test f) (Comparative Test):

90 g dry *Eucalyptus* pulp and 2910 g tap water were mixed using a Pendraulik stirrer at 2000 rpm with a mounted dissolver disk (d=70 mm) for at least 10 minutes. This mixture was processed with the Supermasscolloider as described above in the according paragraph. Samples were taken and measured as described above in the according paragraph.

Test g) (Comparative Test):

Same as test f) but 90 g Omyacarb 1 AV added after fibrillation.

Results

Figure 4:
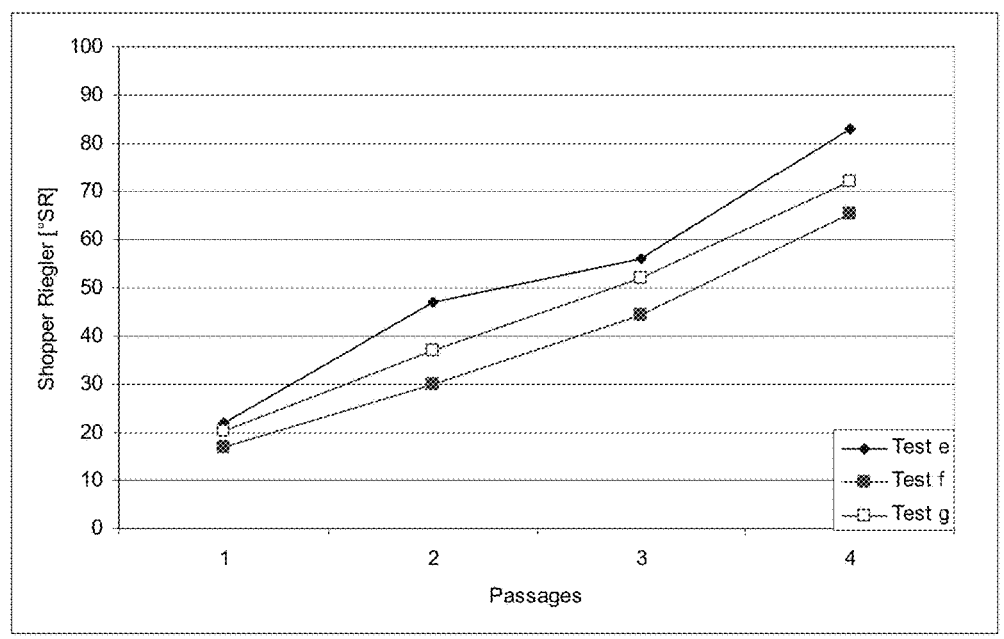
FIG. 4 shows the °SR/running time for pulp suspensions ground with and without natural ground calcium carbonate added before or after fibrillation.

FIG. 4 shows that the addition of filler (test g) to a nanocellulosic suspension that was produced in the absence of filler (test f) leads to increased °SR values, but not to a change of steepness (that means no efficiency increase).

However a nanocellulosic suspension that was produced in the presence of filler (test e) shows a higher increase of °SR compared to the comparative tests (g and f).

6. Use of Nano-Fibrillar Cellulose Suspension in Paper Making 60 g dry of a sulphated paste of wood and fibres composed of 80% birch and 20% pine, with a freeness value of 23°SR, is diluted in 10 dm$^3$ of water. To this dilution is added approximately 1.5 g dry of the nano-fibrillar cellulose suspension produced according to Example 1 using Omyacarb 1-AV, as well as a 62 wt-% suspension of a pre-dispersed natural ground calcium carbonate (marble) having a microcrystalline, rhombohedral particle shape and a weight median particle size $d_{50}$ of 0.8 μm (measured by Sedigraph 5100). The latter is added in an amount so as to obtain an overall filler content of 30+/−0.5% based on the final paper weight. After 15 minutes of agitation and following addition of 0.06% by dry weight, relative to the dry weight of the paper, of a polyacrylamide retention aid, a sheet with a grammage of 75 g/m$^2$ is formed using Rapid-Köthen type hand sheet former.

The invention claimed is:

1. A nano-fibrillar cellulose suspension wherein cellulose fibres are at least partially broken down to primary fibrils obtained by the process comprising the steps of:
   (a) providing cellulose fibres contained in pulps selected from the group consisting of *eucalyptus* pulp, spruce pulp, pine pulp, beech pulp, hemp pulp, cotton pulp, or any mixture thereof;
   (b) providing a filler, wherein the filler is natural ground calcium carbonate, and further wherein the filler has a median particle size of from 0.03 to 15 μm;
   (c) combining the cellulose fibres from step (a) and the filler from step (b); and
   (d) fibrillating the cellulose fibres and the filler from step (c) until the cellulose fibres are partially broken down to primary fibrils and the Schopper Riegler degree is increased at least 4° SR; wherein the fibrillating in step (d) is carried out by a device selected from an ultra-fine friction grinder, a refiner, or a homogenizer, and wherein in step (d) the weight ratio of fibres to filler on a dry weight basis is from 1:10 to 10:1.

2. The suspension according to claim 1, wherein the cellulose fibres in step (a) are contained in kraft pulp.

3. The suspension according to claim 1, wherein the cellulose fibres in step (a) are contained in bleached long-fibre kraft pulp.

4. The suspension according to claim 1, wherein the cellulose fibres in step (a) are provided in the form of a suspension.

5. The suspension according to claim 1, wherein the cellulose fibres in step (a) are provided in the form of a suspension at a solids content of from 0.2 to 35 wt-%.

6. The suspension according to claim 1, wherein the cellulose fibres in step (a) are provided in the form of a suspension at a solids content of from 0.25 to 10 wt.-%.

7. The suspension according to claim 1, wherein the cellulose fibres in step (a) are provided in the form of a suspension at a solids content of from 1 to 5 wt.-%.

8. The suspension according to claim 1, wherein the cellulose fibres in step (a) are provided in the form of a suspension at a solids content of from 2 to 4.5 wt.-%.

9. The suspension according to claim 1, wherein the cellulose fibres in step (a) are provided in the form of a suspension at a solids content of about 1.3 or about 3.5 wt.-%.

10. The suspension according to claim 1, wherein the filler in step (b) is natural ground calcium carbonate selected from marble, limestone and/or chalk.

11. The suspension according to claim 1, wherein the filler in step (b) is in the form of particles having a median particle size of from 0.2 to 5 µm.

12. The suspension according to claim 1, wherein the filler in step (b) is in the form of particles having a median particle size of from 0.2 to 4 µm.

13. The suspension according to claim 1, wherein the filler particles in step (b) is in the form of particles having a median particle size of about 1.5 or about 3.2 µm.

14. The suspension according to claim 1, wherein the filler in step (b) comprises a dispersing agent.

15. The suspension according to claim 14, wherein the dispersing agent is selected from homopolymers or copolymers of polycarboxylic acids and/or their salts or esters, acrylic acid, methacrylic acid, maleic acid, fumaric acid, itaconic acid, acryl amide or acrylic esters, or mixtures thereof; alkali polyphosphates, phosphonic-, citric- or tartaric acids, salts or esters thereof; or mixtures thereof.

16. The suspension according to claim 1, wherein before fibrillating in step (d), the pH of the combination of the cellulose fibres and the filler is adjusted to a pH of 10 to 12.

17. The suspension according to claim 1, wherein after fibrillating in step (d), the pH of the suspension is re-adjusted to a pH of 7.5 to 9.5.

18. The suspension according to claim 1, wherein after fibrillating in step (d), the pH of the suspension is re-adjusted to a pH of about 8.5.

19. The suspension according to claim 1, wherein the combination resulting from step (c) is stored for 2 to 12 hours prior to fibrillating in step (d).

20. The suspension according to claim 1, wherein the combination resulting from step (c) is stored for 3 to 10 hours, prior to fibrillating in step (d).

21. The suspension according to claim 1, wherein the combination resulting from step (c) is stored for 4 to 8 hours, prior to fibrillating in step (d).

22. The suspension according to claim 1, wherein a cellulose solvent is added to the combination in step (c) prior to fibrillating in step (d).

23. The suspension according to claim 22, wherein the cellulose solvent is copper(II)ethylenediamine, iron-sodium-tartrate or lithium-chloride/dimethylacetamide.

24. The suspension according to claim 1, wherein in step (d) the weight ratio of fibres to filler on a dry weight basis is from 1:6 to 6:1.

25. The suspension according to claim 1, wherein in step (d) the weight ratio of fibres to filler on a dry weight basis is from 1:4 to 4:1.

26. The suspension according to claim 1, wherein in step (d) the weight ratio of fibres to filler on a dry weight basis is from 1:3 to 3:1.

27. The suspension according to claim 1, wherein in step (d) the weight ratio of fibres to filler on a dry weight basis is from 1:2 to 2:1.

28. The suspension according to claim 1, wherein the combination from step (c) is fibrillated in step (d) until a Schopper Riegler degree is increased by ≥6° SR.

29. The suspension according to claim 1, wherein the combination from step (c) is fibrillated in step (d) until a Schopper Riegler degree is increased by ≥8° SR.

30. The suspension according to claim 1, wherein the combination from step (c) is fibrillated in step (d) until a Schopper Riegler degree is increased by ≥10° SR.

31. The suspension according to claim 1, wherein the combination from step (c) is fibrillated in step (d) until a Schopper Riegler degree is increased by ≥15° SR.

32. The suspension according to claim 1, wherein the combination of fibres and filler from step (c) is fibrillated in step (d) until a final Schopper-Riegler degree of ≥60° SR is reached.

33. The suspension according to claim 1, wherein the combination of fibres and filler from step (c) is fibrillated in step (d) until a final Schopper-Riegler degree of ≥70° SR is reached.

34. The suspension according to claim 1, wherein the combination of fibres and filler from step (c) is fibrillated in step (d) until a final Schopper-Riegler degree of ≥80° SR is reached.

35. The suspension according to claim 1, wherein the fibrillating in step (d) is carried out by an ultra-fine friction grinder or a homogenizer, and wherein the temperature of the suspension in the ultra-fine friction grinder or the homogenizer is above 60° C.

36. The suspension according to claim 1, wherein the fibrillating in step (d) is carried out by an ultra-fine friction grinder or a homogenizer, and wherein the temperature of the suspension in the ultra-fine friction grinder or the homogenizer is above 80° C.

37. The suspension according to claim 1, wherein the fibrillating in step (d) is carried out by an ultra-fine friction grinder or a homogenizer, and wherein the temperature of the suspension in the ultra-fine friction grinder or the homogenizer is above 90° C.

38. Paper comprising the nano-fibrillar cellulose suspension according to claim 1.

39. A material composite, plastic, paint, rubber, concrete, ceramic, adhesive, food or wound-healing composition comprising the nano-fibrillar cellulose suspension according to claim 1.

* * * * *